(12) United States Patent
Tang et al.

(10) Patent No.: US 10,195,610 B2
(45) Date of Patent: Feb. 5, 2019

(54) CARTRIDGE-BASED THERMOCYCLER

(71) Applicant: Click Diagnostics, Inc., Menlo Park, CA (US)

(72) Inventors: Hamilton R. Tang, Los Altos, CA (US); Adam De La Zerda, Palo Alto, CA (US); Kenneth I. Li, Piedmont, CA (US); Kevin M. Limtao, Temple City, CA (US); Alan D. Baldwin, San Jose, CA (US); Gregory C. Loney, Los Altos, CA (US)

(73) Assignee: Click Diagnostics, Inc., San Jose, CA (US)

( * ) Notice: Subject to any disclaimer, the term of this patent is extended or adjusted under 35 U.S.C. 154(b) by 153 days.

(21) Appl. No.: 15/124,334

(22) PCT Filed: Mar. 9, 2015

(86) PCT No.: PCT/US2015/019497
§ 371 (c)(1),
(2) Date: Sep. 7, 2016

(87) PCT Pub. No.: WO2015/138343
PCT Pub. Date: Sep. 17, 2015

(65) Prior Publication Data
US 2017/0173588 A1 Jun. 22, 2017

Related U.S. Application Data

(60) Provisional application No. 61/950,769, filed on Mar. 10, 2014.

(51) Int. Cl.
*B01L 7/00* (2006.01)
*C12Q 1/6844* (2018.01)
(Continued)

(52) U.S. Cl.
CPC ........... *B01L 7/525* (2013.01); *B01L 3/50273* (2013.01); *B01L 3/502723* (2013.01);
(Continued)

(58) Field of Classification Search
CPC ....................................................... C12Q 1/68
See application file for complete search history.

(56) References Cited

U.S. PATENT DOCUMENTS

| | | | |
|---|---|---|---|
| 3,697,227 A | 10/1972 | Robert et al. | |
| 4,710,355 A | 12/1987 | Ushikubo | |

(Continued)

FOREIGN PATENT DOCUMENTS

| | | |
|---|---|---|
| CN | 101538567 A | 9/2009 |
| CN | 105239164 A | 1/2016 |

(Continued)

OTHER PUBLICATIONS

Advisory Action for U.S. Appl. No. 15/474,083, dated Mar. 26, 2018.
(Continued)

*Primary Examiner* — Aaron A Priest
(74) *Attorney, Agent, or Firm* — Wilson Sonsini Goodrich Rosati

(57) ABSTRACT

Cartridge-based thermocyclers can include cartridges that are configured to move a fluid between distinct chambers. In some cases, the cartridge-based thermocyclers can be used for thermocycling a sample fluid comprising a deoxyribonucleic acid (DNA) target to perform polymerase chain reaction (PCR). Individual chambers can be heated, cooled, and/or compressed to mix fluid within the chamber or to propel fluid in the chamber into another chamber. The cartridges can have a laminate construction. The cartridges can be configured to enable multiplexed thermocycling and/or detection.

22 Claims, 21 Drawing Sheets

(51) Int. Cl.
*B01L 3/00* (2006.01)
*C12Q 1/686* (2018.01)

(52) U.S. Cl.
CPC ........ *B01L 3/502738* (2013.01); *C12Q 1/686* (2013.01); *C12Q 1/6844* (2013.01); *B01L 2300/0816* (2013.01); *B01L 2300/0887* (2013.01); *B01L 2300/123* (2013.01); *B01L 2300/1822* (2013.01); *B01L 2300/1827* (2013.01); *B01L 2400/0478* (2013.01); *B01L 2400/0481* (2013.01); *B01L 2400/0655* (2013.01)

(56) References Cited

U.S. PATENT DOCUMENTS

| | | |
|---|---|---|
| 4,889,692 A | 12/1989 | Holtzman |
| RE33,858 E | 3/1992 | Gropper et al. |
| 5,164,159 A | 11/1992 | Hayashi et al. |
| 5,229,297 A | 7/1993 | Schnipelsky et al. |
| 5,270,183 A | 12/1993 | Corbett et al. |
| 5,273,905 A | 12/1993 | Muller et al. |
| 5,405,585 A | 4/1995 | Coassin |
| 5,429,807 A | 7/1995 | Matson et al. |
| 5,498,392 A | 3/1996 | Wilding et al. |
| 5,631,165 A | 5/1997 | Chupp et al. |
| 5,633,168 A | 5/1997 | Glasscock et al. |
| 5,660,993 A | 8/1997 | Cathey et al. |
| 5,773,234 A | 6/1998 | Pronovost et al. |
| 5,882,903 A | 3/1999 | Andrevski et al. |
| 5,922,591 A | 7/1999 | Anderson et al. |
| 5,952,664 A | 9/1999 | Wake et al. |
| 5,976,470 A | 11/1999 | Maiefski et al. |
| 6,039,924 A | 3/2000 | Horn |
| 6,126,804 A | 10/2000 | Andresen |
| 6,146,591 A | 11/2000 | Miller |
| 6,153,425 A | 11/2000 | Kozwich et al. |
| 6,168,760 B1 | 1/2001 | Horn |
| 6,261,431 B1 | 7/2001 | Mathies et al. |
| 6,303,081 B1 | 10/2001 | Mink et al. |
| 6,313,471 B1 | 11/2001 | Giebeler et al. |
| 6,365,378 B1 | 4/2002 | Hirota et al. |
| 6,374,684 B1 | 4/2002 | Dority |
| 6,416,718 B1 | 7/2002 | Maiefski et al. |
| 6,426,215 B1 | 7/2002 | Sandell |
| 6,514,750 B2 | 2/2003 | Bordenkircher et al. |
| 6,610,499 B1 | 8/2003 | Fulwyler et al. |
| 6,649,378 B1 | 11/2003 | Kozwich et al. |
| 6,656,744 B2 | 12/2003 | Pronovost et al. |
| 6,677,151 B2 | 1/2004 | Sandell |
| 6,680,617 B2 | 1/2004 | Moreland et al. |
| 6,767,512 B1 | 7/2004 | Lurz et al. |
| 6,780,380 B2 | 8/2004 | Hunnell et al. |
| 6,780,617 B2 | 8/2004 | Chen |
| 6,781,056 B1 | 8/2004 | O'Rourke et al. |
| 6,813,568 B2 | 11/2004 | Powell et al. |
| 6,821,771 B2 | 11/2004 | Festoc |
| 6,875,403 B2 | 4/2005 | Liu et al. |
| 6,893,879 B2 | 5/2005 | Petersen et al. |
| 6,901,217 B2 | 5/2005 | Gamboa et al. |
| 6,911,181 B1 | 6/2005 | McNeil |
| 6,964,862 B2 | 11/2005 | Chen |
| 6,990,290 B2 | 1/2006 | Kylberg et al. |
| 7,041,481 B2 | 5/2006 | Anderson et al. |
| 7,144,742 B2 | 12/2006 | Boehringer et al. |
| 7,179,639 B2 | 2/2007 | Pottathil et al. |
| 7,189,522 B2 | 3/2007 | Esfandiari |
| 7,192,721 B1 | 3/2007 | Esfandiari et al. |
| 7,235,216 B2 | 6/2007 | Kiselev et al. |
| 7,297,313 B1 | 11/2007 | Northrup et al. |
| 7,341,697 B2 | 3/2008 | Takeuchi et al. |
| 7,377,291 B2 | 5/2008 | Moon et al. |
| 7,378,285 B2 | 5/2008 | Lambotte et al. |
| 7,384,782 B2 | 6/2008 | Nakatani et al. |
| 7,416,892 B2 | 8/2008 | Battrell et al. |
| 7,438,852 B2 | 10/2008 | Tung et al. |
| 7,459,302 B2 | 12/2008 | Reid et al. |
| 7,491,551 B2 | 2/2009 | Boehringer et al. |
| 7,517,495 B2 | 4/2009 | Wu et al. |
| 7,544,324 B2 | 6/2009 | Tung et al. |
| 7,550,112 B2 | 6/2009 | Gou et al. |
| 7,553,675 B2 | 6/2009 | Jerome et al. |
| 7,569,382 B2 | 8/2009 | Li |
| 7,579,172 B2 | 8/2009 | Cho et al. |
| 7,592,139 B2 | 9/2009 | West et al. |
| 7,632,687 B2 | 12/2009 | Gokhan |
| 7,648,835 B2 | 1/2010 | Breidford et al. |
| 7,682,801 B2 | 3/2010 | Esfandiari |
| 7,691,644 B2 | 4/2010 | Lambotte et al. |
| 7,705,339 B2 | 4/2010 | Smith et al. |
| 7,709,250 B2 | 5/2010 | Corbett et al. |
| 7,754,452 B2 | 7/2010 | Kim et al. |
| 7,767,439 B2 | 8/2010 | Oh et al. |
| 7,794,656 B2 | 9/2010 | Liang et al. |
| 7,799,521 B2* | 9/2010 | Chen .................. B01L 3/502 435/286.5 |
| 7,837,939 B2 | 11/2010 | Tung et al. |
| 7,858,396 B2 | 12/2010 | Corstjens et al. |
| 7,871,568 B2 | 1/2011 | Liang et al. |
| 7,879,293 B2 | 2/2011 | Niedbala et al. |
| 7,914,986 B2 | 3/2011 | Nunn |
| 7,915,013 B2 | 3/2011 | Cho et al. |
| 7,935,504 B2 | 5/2011 | Chen |
| 7,943,348 B2 | 5/2011 | Cho et al. |
| 7,959,877 B2 | 6/2011 | Esfandiari |
| 7,985,716 B2 | 7/2011 | Yershov et al. |
| 7,988,915 B2 | 8/2011 | Lee et al. |
| 7,998,757 B2 | 8/2011 | Darrigrand et al. |
| 8,008,046 B2 | 8/2011 | Maltezos et al. |
| 8,008,080 B2 | 8/2011 | Tokhtuev et al. |
| 8,012,427 B2 | 9/2011 | Bommarito et al. |
| 8,018,593 B2 | 9/2011 | Tan et al. |
| 8,048,386 B2 | 11/2011 | Dority et al. |
| 8,062,883 B2 | 11/2011 | Woudenberg et al. |
| 8,075,854 B2 | 12/2011 | Yang et al. |
| 8,076,129 B2 | 12/2011 | Hanafusa et al. |
| 8,088,616 B2 | 1/2012 | Handique |
| 8,110,148 B2 | 2/2012 | Ball et al. |
| 8,110,392 B2 | 2/2012 | Battrell et al. |
| 8,133,671 B2 | 3/2012 | Williams et al. |
| 8,133,703 B2 | 3/2012 | Ching et al. |
| 8,148,116 B2 | 4/2012 | Chen |
| 8,163,489 B2 | 4/2012 | Murray et al. |
| 8,163,535 B2 | 4/2012 | Reed et al. |
| 8,169,610 B2 | 5/2012 | Oldham et al. |
| 8,173,077 B2 | 5/2012 | Korampally et al. |
| 8,187,557 B2 | 5/2012 | Van Atta et al. |
| 8,198,074 B2 | 6/2012 | Moriwaki et al. |
| 8,216,832 B2 | 7/2012 | Battrell et al. |
| 8,222,023 B2 | 7/2012 | Battrell et al. |
| 8,231,844 B2 | 7/2012 | Gorfinkel et al. |
| 8,232,091 B2 | 7/2012 | Maltezos et al. |
| 8,232,094 B2 | 7/2012 | Hasson et al. |
| 8,247,221 B2 | 8/2012 | Fawcett |
| 8,263,392 B2 | 9/2012 | Gale et al. |
| 8,277,763 B2 | 10/2012 | Steinmann et al. |
| 8,278,091 B2 | 10/2012 | Rutter et al. |
| 8,298,763 B2 | 10/2012 | Regan |
| 8,323,583 B2 | 12/2012 | Gou et al. |
| 8,329,453 B2 | 12/2012 | Battrell et al. |
| 8,343,442 B2 | 1/2013 | McBride et al. |
| 8,343,754 B2 | 1/2013 | Wittwer et al. |
| 8,357,490 B2 | 1/2013 | Froehlich et al. |
| 8,372,340 B2 | 2/2013 | Bird et al. |
| 8,389,960 B2 | 3/2013 | Pieprzyk et al. |
| 8,394,322 B2 | 3/2013 | Windeyer et al. |
| 8,394,608 B2 | 3/2013 | Ririe et al. |
| 8,394,626 B2 | 3/2013 | Ramsey et al. |
| 8,426,134 B2 | 4/2013 | Piepenburg et al. |
| 8,431,413 B2 | 4/2013 | Dority et al. |
| 8,435,461 B2 | 5/2013 | Kirby et al. |
| 8,448,824 B2 | 5/2013 | Diperna |
| 8,492,136 B2 | 7/2013 | Carlisle et al. |
| 8,507,259 B2 | 8/2013 | Esfandiari |

(56) References Cited

U.S. PATENT DOCUMENTS

| | | |
|---|---|---|
| 8,580,575 B2 | 11/2013 | Hanafusa |
| 8,597,937 B2 | 12/2013 | Ward et al. |
| 8,603,835 B2 | 12/2013 | Esfandiari |
| 8,617,486 B2 | 12/2013 | Kirby et al. |
| 8,629,264 B2 | 1/2014 | Reed et al. |
| 8,637,250 B2 | 1/2014 | Jenison |
| 8,663,976 B2 | 3/2014 | Chung et al. |
| 8,673,238 B2 | 3/2014 | Dority et al. |
| 8,673,239 B2 | 3/2014 | Niedbala et al. |
| 8,691,561 B2 | 4/2014 | Igata |
| 8,722,426 B2 | 5/2014 | Lambotte et al. |
| 8,728,765 B2 | 5/2014 | Ching et al. |
| 8,735,103 B2 | 5/2014 | Chung et al. |
| 8,758,701 B2 | 6/2014 | Van Atta et al. |
| 8,765,454 B2 | 7/2014 | Zhou et al. |
| 8,772,017 B2 | 7/2014 | Battrell et al. |
| 8,795,592 B2 | 8/2014 | Eiriksson |
| 8,859,199 B2 | 10/2014 | Hellyer et al. |
| 8,865,458 B2 | 10/2014 | Ramsey et al. |
| 8,871,155 B2 | 10/2014 | Wu et al. |
| 8,877,450 B2 | 11/2014 | Esfandiari |
| 8,894,946 B2 | 11/2014 | Nielsen et al. |
| 8,900,828 B2 | 12/2014 | Smith et al. |
| 8,900,853 B2 | 12/2014 | Verhaar et al. |
| 8,911,941 B2 | 12/2014 | Michlitsch |
| 8,911,949 B2 | 12/2014 | Bertrand et al. |
| 8,916,375 B2 | 12/2014 | Landers et al. |
| 8,945,843 B2 | 2/2015 | Alvino et al. |
| 8,975,027 B2 | 3/2015 | Gale et al. |
| 8,980,177 B2 | 3/2015 | Carlisle et al. |
| 8,980,561 B1 | 3/2015 | Cai et al. |
| 8,986,927 B2 | 3/2015 | Lee et al. |
| 8,992,854 B2 | 3/2015 | Brewster et al. |
| 9,011,770 B2 | 4/2015 | Wu et al. |
| 9,012,236 B2 | 4/2015 | Jovanovich et al. |
| 9,023,639 B2 | 5/2015 | Kim et al. |
| 9,044,729 B2 | 6/2015 | Rengifo et al. |
| 9,207,236 B2 | 12/2015 | Cary |
| 9,207,241 B2 | 12/2015 | Lambotte et al. |
| 9,243,288 B2 | 1/2016 | Colston, Jr. et al. |
| 9,428,781 B2 | 8/2016 | Cai et al. |
| 9,475,049 B2 | 10/2016 | Siciliano et al. |
| D776,290 S | 1/2017 | Wan et al. |
| 9,623,415 B2 | 4/2017 | Andreyev et al. |
| 2001/0055799 A1 | 12/2001 | Baunoch et al. |
| 2002/0086417 A1 | 7/2002 | Chen |
| 2003/0027244 A1 | 2/2003 | Colston et al. |
| 2004/0110141 A1 | 6/2004 | Pusey et al. |
| 2004/0209331 A1* | 10/2004 | Ririe ............ B01L 3/502 435/91.2 |
| 2004/0224317 A1 | 11/2004 | Kordunsky et al. |
| 2004/0251426 A1 | 12/2004 | Birk et al. |
| 2005/0019875 A1 | 1/2005 | Chen |
| 2005/0064598 A1 | 3/2005 | Yuan et al. |
| 2005/0227275 A1 | 10/2005 | Jung et al. |
| 2006/0001689 A1 | 1/2006 | Ahne et al. |
| 2006/0088931 A1 | 4/2006 | Ririe |
| 2006/0154341 A1 | 7/2006 | Chen |
| 2006/0160205 A1 | 7/2006 | Blackburn et al. |
| 2006/0246493 A1 | 11/2006 | Jensen et al. |
| 2007/0026391 A1 | 2/2007 | Stoughton et al. |
| 2007/0042427 A1 | 2/2007 | Gerdes et al. |
| 2007/0154922 A1 | 7/2007 | Collier et al. |
| 2007/0284360 A1 | 12/2007 | Santoruvo et al. |
| 2007/0292941 A1 | 12/2007 | Handique et al. |
| 2008/0026451 A1 | 1/2008 | Braman et al. |
| 2008/0038737 A1 | 2/2008 | Smith et al. |
| 2008/0043235 A1 | 2/2008 | Oldham et al. |
| 2008/0050735 A1 | 2/2008 | Pushnova |
| 2008/0057572 A1 | 3/2008 | Petersen et al. |
| 2008/0145852 A1 | 6/2008 | Shuber |
| 2008/0153078 A1 | 6/2008 | Braman et al. |
| 2008/0220468 A1 | 9/2008 | Windeyer et al. |
| 2008/0274513 A1* | 11/2008 | Shenderov ........ B01L 3/502792 435/91.2 |
| 2008/0280285 A1 | 11/2008 | Chen et al. |
| 2009/0029422 A1 | 1/2009 | Hanafusa et al. |
| 2009/0042256 A1 | 2/2009 | Hanafusa et al. |
| 2009/0130745 A1 | 5/2009 | Williams et al. |
| 2009/0186344 A1 | 7/2009 | Farinas |
| 2009/0215072 A1 | 8/2009 | McDevitt et al. |
| 2009/0325276 A1 | 12/2009 | Battrell et al. |
| 2010/0113762 A1 | 5/2010 | Ball et al. |
| 2010/0173393 A1 | 7/2010 | Handique et al. |
| 2010/0210038 A1 | 8/2010 | Blatt et al. |
| 2010/0291588 A1 | 11/2010 | McDevitt et al. |
| 2010/0297640 A1 | 11/2010 | Kumar et al. |
| 2011/0039303 A1 | 2/2011 | Jovanovich et al. |
| 2011/0160090 A1 | 6/2011 | Cary |
| 2011/0203688 A1 | 8/2011 | Reed et al. |
| 2011/0207121 A1 | 8/2011 | Chen |
| 2011/0211331 A1 | 9/2011 | Alkjaer et al. |
| 2011/0227551 A1 | 9/2011 | Black |
| 2011/0269191 A1 | 11/2011 | Belgrader et al. |
| 2011/0300545 A1 | 12/2011 | Cano et al. |
| 2011/0312666 A1 | 12/2011 | Azimi et al. |
| 2011/0312793 A1 | 12/2011 | Azimi et al. |
| 2011/0313148 A1 | 12/2011 | Christ et al. |
| 2012/0021454 A1 | 1/2012 | Bikker et al. |
| 2012/0064534 A1 | 3/2012 | Pipper et al. |
| 2012/0070878 A1 | 3/2012 | Fink et al. |
| 2012/0088294 A1 | 4/2012 | Sun et al. |
| 2012/0115738 A1 | 5/2012 | Zhou et al. |
| 2012/0130061 A1 | 5/2012 | Himmelreich et al. |
| 2012/0135511 A1 | 5/2012 | Battrell et al. |
| 2012/0141337 A1 | 6/2012 | Maltezos et al. |
| 2012/0237939 A1 | 9/2012 | Reed et al. |
| 2012/0264202 A1 | 10/2012 | Walker et al. |
| 2012/0276532 A1 | 11/2012 | Chen |
| 2012/0282684 A1 | 11/2012 | Fritchie et al. |
| 2012/0288897 A1 | 11/2012 | Ching et al. |
| 2013/0053255 A1 | 2/2013 | Vangbo et al. |
| 2013/0059290 A1 | 3/2013 | Armes |
| 2013/0078736 A1 | 3/2013 | Grover et al. |
| 2013/0115712 A1 | 5/2013 | Yu et al. |
| 2013/0118900 A1 | 5/2013 | Reimitz et al. |
| 2013/0149710 A1 | 6/2013 | Yoon et al. |
| 2013/0171640 A1 | 7/2013 | Kwon et al. |
| 2013/0210080 A1 | 8/2013 | Rajagopal et al. |
| 2013/0217026 A1 | 8/2013 | Egan et al. |
| 2013/0220781 A1 | 8/2013 | Czarnecki |
| 2014/0045191 A1 | 2/2014 | Dejohn et al. |
| 2014/0051159 A1 | 2/2014 | Bergstedt et al. |
| 2014/0098252 A1 | 4/2014 | Chang et al. |
| 2014/0120539 A1 | 5/2014 | Tanner et al. |
| 2014/0199685 A1 | 7/2014 | Lambotte et al. |
| 2014/0274770 A1 | 9/2014 | Pack |
| 2015/0031087 A1 | 1/2015 | Nagai et al. |
| 2015/0176057 A1 | 6/2015 | Smith et al. |
| 2015/0182966 A1 | 7/2015 | Coursey et al. |
| 2015/0240298 A1 | 8/2015 | Piepenburg et al. |
| 2015/0258273 A1 | 9/2015 | Payne et al. |
| 2015/0322483 A1 | 11/2015 | Nakamura et al. |
| 2015/0346097 A1 | 12/2015 | Battrell et al. |
| 2015/0361419 A1 | 12/2015 | Kim et al. |
| 2016/0054316 A1 | 2/2016 | Egan et al. |
| 2016/0186240 A1 | 6/2016 | Andreyev et al. |
| 2016/0222442 A1 | 8/2016 | Cary |
| 2016/0310948 A1 | 10/2016 | Nowakowski et al. |
| 2017/0173588 A1 | 6/2017 | Tang et al. |
| 2017/0203297 A1 | 7/2017 | Andreyev et al. |
| 2017/0247745 A1 | 8/2017 | Shultz et al. |
| 2017/0259263 A1 | 9/2017 | Andreyev et al. |
| 2017/0304829 A1 | 10/2017 | Andreyev et al. |
| 2018/0071734 A1 | 3/2018 | Andreyev et al. |
| 2018/0117590 A1 | 5/2018 | Andreyev et al. |

FOREIGN PATENT DOCUMENTS

| | | |
|---|---|---|
| EP | 1347833 B1 | 10/2011 |
| EP | 2614147 A1 | 7/2013 |
| WO | WO-0149416 A1 | 7/2001 |
| WO | WO-2008149111 A1 | 12/2008 |
| WO | WO-2009047804 A2 | 4/2009 |

(56) References Cited

FOREIGN PATENT DOCUMENTS

| WO | WO-2014035986 A1 | 3/2014 |
| WO | WO-2014144548 A2 | 9/2014 |
| WO | WO-2015138343 A1 | 9/2015 |
| WO | WO-2015138648 A1 | 9/2015 |
| WO | WO-2015164770 A1 | 10/2015 |
| WO | WO-2016040523 A1 | 3/2016 |
| WO | WO-2016109691 A1 | 7/2016 |
| WO | WO-2016203019 A1 | 12/2016 |
| WO | WO-2017197040 A1 | 11/2017 |
| WO | WO-2018005870 A1 | 1/2018 |

OTHER PUBLICATIONS

Final Office Action for U.S. Appl. No. 15/474,083, dated Jan. 25, 2018.

Gehring, et al., A High-Throughput, Precipitating Colorimetric Sandwich ELISA Microarray for Shiga Toxins, J. Toxins, vol. 6, p. 1855-72, Jun. 11, 2014.

Hwang et al., "Black Printed Circuit Board-based Micro-Polymerase Chain Reaction Chip Structure for Fluorescence Detection Test", International Journal of Control and Automation, 8(10):15-24, 2015.

Interbiotech, "Enzymatic substrates for ImmunoAssays," [retrieved from the Internet Nov. 18, 2017:< http://www.interchim.fr/ft/B/BA357a.pdf], 10 pages.

International Search Report and Written Opinion for International Application No. PCT/US2017/029004, dated Aug. 23, 2017.

International Search Report and Written Opinion for International Application No. PCT/US2017/039844, dated Dec. 7, 2017.

Kim, et al., Automated microfluidic DNA/RNA extraction with both disposable and reusable components. Journal of Micromechanics and Microengineering, Dec. 2011; 22(1):pp. 6,8,11.

Lee, et al., A polymer lab-on-a-chip for reverse transcription (RT)-PCR based point-of-care clinical diagnostics. The Royal Society of Chemistry, Oct. 2008; 8:2121-27.

Mohammed, et al., Modelling of Serpentine Continuous Flow Polymerase Chain Reaction Microfluidics. IJEST, Mar. 2012; 4(3), pp. 1183-1189.

Non-final Office Action for U.S. Appl. No. 15/474,083, dated Aug. 24, 2017.

Office Action for U.S. Appl. No. 15/586,780, dated Feb. 6, 2018.

PCT/US2015/049247 International Preliminary Report on Patentability dated Mar. 14, 2017.

PCT/US2015/068101 International Preliminary Report on Patentability dated Jul. 13, 2017.

PCT/US2017/032035 International Search Report and Written Opinion dated Oct. 4, 2017.

PCT/US2017/040112 International Search Report and Written Opinion dated Nov. 9, 2017.

Thiha, et al., A Colorimetric Enzyme-Linked Immunosorbent Assay (ELISA) Detection Platform for a Point-of-Care Dengue Detection System on a Lab-on-Compact-Disc. Sensors (Basel). May 18, 2015;15(5):11431-41. doi: 10.3390/s150511431.

BioFire Online Demo FilmArray. http://filmarray.com/the-evidence/online-demo. 2014, 6 pages.

Koop et al., Chemical amplification: Continuous-flow PCR on a chip Science, 280(5366):1046-1048, 1998.

PCT Patent Application No. PCT/US2015/019497 International Search Report and Written Opinion dated Jun. 8, 2015.

PCT Patent Application No. PCT/US2015/049247 International Search Report and Written Opinion dated Jan. 12, 2016.

PCT/US2015/019497 International Preliminary Report on Patentability dated Sep. 13, 2016.

PCT/US2015/068101 International Search Report and Written Opinion dated May 5, 2016.

Schwerdt. Application of ferrofluid as a valve/pump for polycarbonate microfluidic devices. Johns Hopkins University. NSF Summer Undergraduate Fellowship in Sensor Technologies 2006, 17 pages.

Tanriverdi, et al. A rapid and automated sample-to-result HIV load test for near-patient application. J Infect Dis., 201 Suppl 1:S52-S58, 2010.

U.S. Appl. No. 14/984,573 First Action Interview Pilot Program Pre-Interview Communication dated Aug. 16, 2016.

\* cited by examiner

A.

B.

CARTRIDGE-BASED THERMOCYCLER

CROSS-REFERENCE

This application claims the benefit of U.S. Provisional Application No. 61/950,769 filed Mar. 10, 2014 entitled "CARTRIDGE-BASED THERMOCYCLER", which is incorporated by reference herein in its entirety.

SUMMARY

The present disclosure provides systems for performing thermal cycling (also "thermocycling" herein) of a fluid (also "sample" or "sample fluid" herein). The systems herein can be used for thermocycling a sample fluid to perform biological or biochemical analysis. In some examples, the systems herein can be used for thermocycling a sample fluid comprising a deoxyribonucleic acid (DNA) target to perform polymerase chain reaction (PCR). The systems can be cartridge-based systems (also "cartridges," "cartridge-based thermocyclers" or "cassettes" herein) that enable low-cost, disposable PCR systems to be realized. In some cases, the cartridges can be real-time, multiplexed systems (also "multiplexed assays" herein). The cartridges can be coupled to other PCR system components, such as, for example, one or more other cartridges and/or an instrument. In some implementations, PCR systems comprising disposable cartridge system(s) coupled with a durable instrument can be provided.

Systems of the present disclosure include cartridges that are configured to move fluid between distinct chambers. Each chamber can have a given temperature, composition, volume and/or shape. Individual chambers can be heated, cooled, and/or compressed to mix fluid within the chamber or to propel fluid in the chamber into another chamber. Further, the chambers can be shaped to inhibit trapping of air bubbles. The chambers can be configured to allow rapid thermal equilibration. In some implementations, the cartridge comprising the chambers can have a laminate construction.

The present disclosure relates to a thermocycler comprising a first chamber for holding a fluid at a first average temperature and a second chamber for holding the fluid at a second average temperature. The second chamber is in fluid communication with the first chamber, wherein the fluid is transferred between the first chamber and the second chamber to achieve a transition from the first average temperature to substantially the second average temperature or vice versa at a rate of 10 µL° C./second or more. The first and second chambers can be provided on a disposable portion of the thermocycler. In some cases, the transition from the first average temperature to substantially the second average temperature or vice versa can be achieved at a rate of 25 µL° C./second or more. The thermocycler can have a cycle time of 10 seconds or less. The fluid can have a starting volume of about 25 µL or more. In one embodiment, the first average temperature is nominally between about 55° C. (328 K) and about 65° C. (338 K), and the second average temperature is nominally about 95° C. (368 K). In one embodiment, the fluid has a starting volume of about 25 µL or more, for example, about µL. In one embodiment, the fluid is transferred between the first chamber and the second chamber to achieve the transition from the first average temperature to substantially the second average temperature or vice versa within 5 seconds or less, 4 seconds or less, 3 seconds or less, 2 seconds or less, or 1 second or less. In one embodiment, the thermocycler comprises a filling and/or venting channel, wherein the venting channel prevents gases from being trapped during filling.

The present disclosure is directed to a method for performing polymerase chain reaction (PCR) comprising providing a first fluid holding chamber having a first average temperature, providing a second fluid holding chamber having a second average temperature, mechanically actuating fluid transfer between the first chamber and the second chamber, and completing the PCR within a total thermocycling time that is at least about 9 times shorter than a corresponding thermocycling time on a conventional system. The method can further comprise completing the PCR amplification within a total thermocycling time of less than about 4 minutes. The method can further comprise completing the PCR within a total thermocycling time that is at least about 11.5 times shorter than the corresponding thermocycling time on a conventional system. The method can further comprise completing the PCR at a PCR efficiency that is substantially the same as a PCR efficiency of the conventional system. The PCR efficiency can be at least about 92%. In one embodiment, the method further comprises detecting PCR amplification by monitoring the first chamber, the second chamber or a channel between the first chamber and the second chamber. Monitoring includes optical multiplexing. In one embodiment, a PCR amplification method is completed in a time that is about 11.5 times shorter than the corresponding thermocycling time on a conventional system. In one instance, the PCR efficiency is substantially the same as a PCR efficiency of the conventional system. In another instance, the PCR amplification is equal to an amplification of the conventional system. In one embodiment, the PCR method is complete upon reaching a predetermined number of cycles.

The present disclosure provides a low-cost polymerase chain reaction (PCR) system comprising a cartridge configured for transferring a fluid between a first chamber and a second chamber maintained at distinct temperatures, wherein the cartridge has a laminate construction defining the first chamber and the second chamber, and wherein the transfer of the fluid between the first chamber and the second chamber is for thermocycling the fluid. The laminate construction can define the first chamber and the second chamber in the absence of mechanical force or mechanical actuation. In one embodiment, the cartridge is disposable. In one embodiment, the volumes of the first chamber and the second chamber depend on the thickness of individual layers of the laminate construction. In one implementation, the laminate construction comprises a first outer plastic layer, a first pressure sensitive adhesive layer, a second pressure sensitive adhesive layer, a second outer plastic layer, and optionally a cover. In one embodiment, the cover is a rigid structure. In one embodiment, the cover is bonded to the first outer plastic layer or the second outer plastic layer. In another embodiment, the first outer plastic layer or the second outer plastic layer is a membrane layer. In one embodiment, the starting volume of the fluid is at least about 25 µL, at least about 50 µL, and/or at least about 60 µL. In one embodiment, the height of the first chamber and the second chamber is 250 µm or less. In one embodiment, the first chamber or the second chamber has a tear drop shape. In another embodiment, the first chamber or the second chamber or both are shaped to achieve a reduced number of nucleation sites.

In one embodiment, the low-cost polymerase chain reaction (PCR) system has a laminate construction comprising an optical window. In one embodiment, the optical window provides an optical path to a portion of a fluid path between the first chamber and the second chamber. In one embodiment, a sample volume is interrogated through the optical window. In another embodiment, the optical window comprises a light directing feature. A light directing feature includes, without limitation, a lens, prism, Fresnel lens or any combination thereof. In a further embodiment, the system further comprises a blocking feature to obstruct stray light from an excitation source. Blocking features include, without limitation, foil, coatings or a combination thereof.

The present disclosure further provides a multiplexed assay comprising a plurality of thermocycling units. Each thermocycling unit comprises a first chamber for holding a fluid at a first average temperature. Each thermocycling unit further comprises a second chamber for holding the fluid at a second average temperature. The second chamber is in fluid communication with the first chamber. The first chamber and the second chamber each have a non-zero volume prior to holding the fluid. In one embodiment, the assay further comprises a detector coupled to at least a subset of the plurality of thermocycling units. In one embodiment, the detector is dedicated to a single thermocycling unit of the plurality of thermocycling units. In one embodiment, the detector is shared by at least a subset of the plurality of thermocycling units. In one embodiment, at least a subset of the plurality of thermocycling units are identical. In another embodiment, a first subset of the plurality of thermocycling units has a different configuration than a second subset of the plurality of thermocycling units.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

Figure 1:
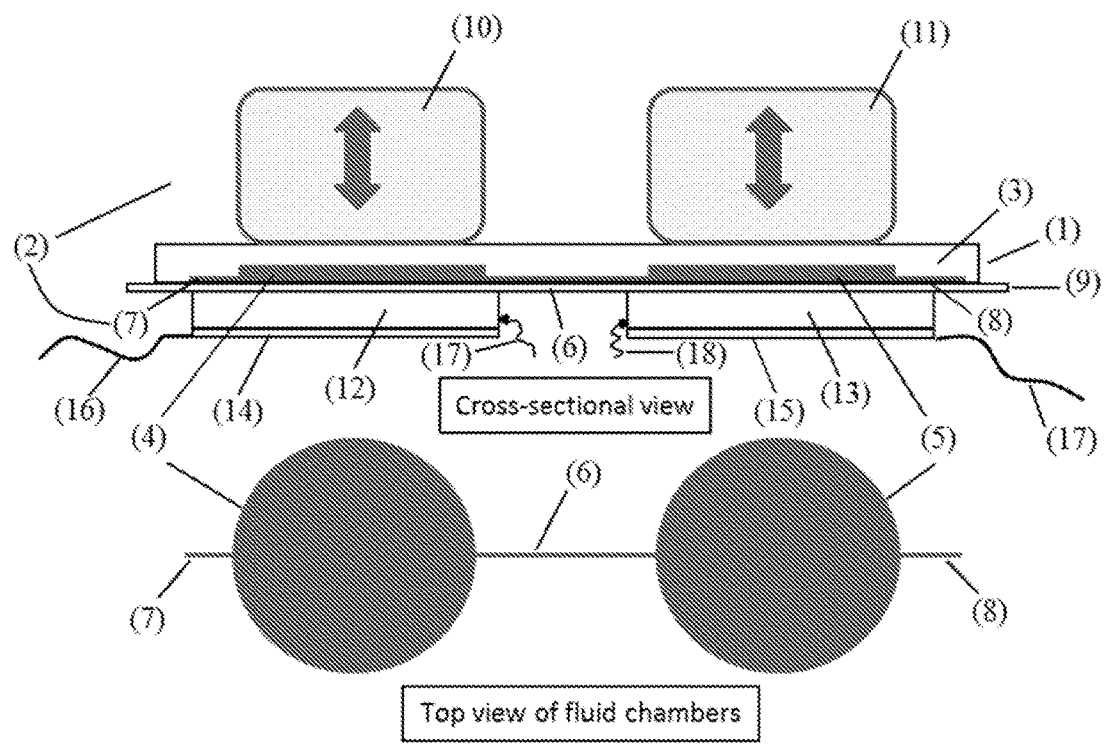
FIG. 1 shows a cross-sectional view of a thermocycling unit and a top view of fluid chambers on the thermocycling unit.

While various embodiments of the invention have been shown and described herein, it will be obvious to those skilled in the art that such embodiments are provided by way of example only. Numerous variations, changes, and substitutions occurs to those skilled in the art without departing from the invention. It should be understood that various alternatives to the embodiments of the invention described herein are employable. It shall be understood that different aspects of the invention can be appreciated individually, collectively, or in combination with each other.

The term "polymerase chain reaction (PCR)," as used herein, generally refers to any variation on the basic process or operation of amplifying a single or a few copies of a specific region of a DNA strand (also referred to as "DNA target," "target," or "target DNA" herein) to generate copies of a particular DNA sequence. In some examples, DNA fragments of between about 100 and 40,000 base pairs (bp) can be amplified. Primers (e.g., short DNA fragments) containing sequences complementary to the target region along with a DNA polymerase (e.g., Taq polymerase or another heat-stable DNA polymerase) can be provided to enable selective and repeated amplification. As PCR progresses, the DNA generated can itself be used as a template for replication. Components needed to perform PCR can include, but are not limited to, primers, DNA polymerase, DNA building blocks (e.g., deoxynucleoside triphosphate nucleotides), buffer solution, divalent cations (e.g., magnesium or manganese ions), and monovalent cations (e.g., potassium ions). Thermal cycling (e.g., alternate heating and cooling of the PCR sample) through a defined series of temperature steps can be used. In some examples, a series of 20-40 repeated temperature changes (also "cycles" herein) can be used, with each cycle comprising two or three discrete temperature steps, as described in greater detail below. In some cases, the cycling can be preceded by and/or followed by additional temperature step(s). The temperatures used and the length of time they are applied in each cycle can depend on a variety of parameters (e.g., enzyme used for DNA synthesis, concentration of divalent ions and nucleotides in the reaction, melting temperature of the primers).

The term "amplification," as used herein, generally refers to a relationship between an amplified target concentration and an initial target concentration. The amplification can be defined as, for example, $A=C_x/C_0$, where $C_x$ is the amplified target concentration (e.g., DNA copies per volume) and $C_0$ is the initial target concentration (e.g., DNA copies per volume). In an example, an initial concentration of *Bacillus Atrophaeus* (B. Atro) DNA of about $C_0=10^5$ copies per milliliter (mL) is run through 30 cycles of PCR thermocycling to achieve an amplified target concentration of about $C_x=10^{13}$ copies/mL, and thus an amplification of about $A=10^8$. At a PCR efficiency of 100%, each cycle can double the target population, and at 30 cycles, an amplification of about $2^{30}$ or about $A=10^9$ can be achieved. Since the amplification in this example is less than $10^9$, the PCR efficiency is less than 100%. For example, the PCR efficiency can be about 84% or about 92%. In some examples, PCR can continue to a given amplification, where a target population (also "target concentration" herein) is easily observed (e.g., by observing an optical signal produced by a bound fluorescent probe). In some examples, reaching a given number of cycles can be used to define completion of the PCR (i.e., PCR completion can be defined as a point when a given number of cycles have been completed). Amplification includes, without limitation, nucleic acid amplification. Exemplary nucleic acid amplification reactions include, without limitation, polymerase chain reaction (PCR), strand displacement amplification (SDA), helicase dependent amplification (HDA), loop-mediated isothermal amplification (LAMP), transcription-mediated amplification (TMA), nucleic acid sequence based amplification (NASBA) and self-sustained sequence replication (3SR). Nucleic acid amplification reactions include both real-time and end-point reactions.

The term "cycle time," as used herein, generally refers to the time required to accomplish a denaturing step, an annealing step, and an extension step in a nucleic acid amplification reaction. In an exemplary embodiment, these steps are done at three distinct temperatures or two distinct temperatures. In an example where these steps are accomplished at two distinct temperatures in two respective cartridge chambers, the cycle time is the residence time of a sample in two consecutive chambers (e.g., a hot chamber and a cold chamber) of a cartridge.

The term "ramp time," as used herein, generally refers to the time required for the bulk of a fluid to ramp from a first temperature to a second temperature.

The term "extension time," as used herein, generally refers to the time required for a DNA polymerase (e.g., Taq polymerase) to extend the length of the copied molecule. A typical extension rate for Taq polymerase can be 1000 nucleotides per second at 72° C. The extension time for a PCR product on the order of 200-400 bp using the cartridge-based thermocyclers of the present disclosure can be, for example, 1-2 seconds.

The term "melt time," as used herein, generally refers to the time required to achieve adequate melting of the DNA of the copied molecule (e.g., by disrupting hydrogen bonds between complementary bases, yielding single-stranded DNA molecules).

The term "dwell time," as used herein, generally refers to the time that a sample resides at each temperature. For example, for two-temperature PCR, cycle time can equal the dwell time times two. In some cases, cycle time can be a sum of a first dwell time at a first temperature and a second dwell time at a second temperature. In an example, the dwell time equals the residence time of a sample in an individual chamber (e.g., a hot chamber or a cold chamber) of a cartridge. In some cases, dwell time can equal ramp time plus extension time (e.g., in a cold chamber). In some cases, dwell time can equal ramp time plus melt time (e.g., in a hot chamber). In some cases, the melt time can be less than the extension time. Thus, dwell times based on ramp time plus extension time can provide an upper limit for dwell times in both hot side and cold side chambers. In an example, the dwell time using the cartridge-based thermocyclers of the present disclosure can be 5 seconds and can include 3 seconds of ramp time and 2 seconds of extension time.

In various implementations, a reference to time (including, but not limited to, cycle time, ramp time, extension time, melt time, dwell time) in a nucleic acid amplification cycle is dependent, at least in part, on the number of nucleic acids to be amplified, the sequence of nucleic acids to be amplified, the oligonucleotide primers used in the amplification reaction, and any combination thereof. In one embodiment, the thermocyclers and methods provided herein are useful for amplifying a nucleic acid comprising between about 50 base pairs (bp) and about 50,000 bp, between about 50 bp and about 40,000 bp, between about 50 bp and about 30,000 bp, between about 50 bp and about 20,000 bp, between about 50 bp and about 10,000 bp, or between about 50 bp and about 5,000 bp. In one embodiment, the thermocyclers and methods provided herein are useful for amplifying a nucleic acid comprising between about 50 bp and about 5,000 bp, between about 50 bp and about 4,000 bp, between about 50 bp and about 3,000 bp, between about 50 bp and about 2,000 bp, between about 50 bp and about 1,000 bp, or between about 50 bp and about 500 bp. In another embodiment, the thermocyclers and methods provided herein are useful for amplifying a nucleic acid comprising between about 50 base pairs bp and about 500 bp, between about 50 bp and about 400 bp, between about 50 bp and about 300 bp, between about 50 bp and about 200 bp, between about 100 bp and about 1,000 bp, between about 100 bp and about 500 bp, between about 100 bp and about 400 bp, between about 100 bp and about 300 bp, between about 150 bp and about 1,000 bp, between about 150 bp and about 500 bp, between about 150 bp and about 400 bp, or between about 150 bp and about 300 bp. In one embodiment, the nucleic acid amplification for a nucleic acid template comprising from about 50 bp to about 5,000 bp is at least about 90%, 91%, 92%, 93%, 94%, 95%, 96%, 97%, 98% or more efficient. In one embodiment, a nucleic acid amplification cycle time for a nucleic acid template comprising from about 50 bp to about 5,000 bp is less than about 60 seconds, less than about 50 seconds, less than about 40 seconds, less than about 30 seconds, less than about 20 seconds, less than about 10 seconds, or less than about 5 seconds.

Cartridge-Based Rapid Thermocyclers

The disclosure provides systems for performing thermal cycling (also "thermocycling" herein) of a fluid (also "sample" or "sample fluid" herein). The systems herein can be used for thermocycling a sample fluid to perform biological or biochemical analysis. In some examples, the systems herein can be used for thermocycling a sample fluid comprising a deoxyribonucleic acid (DNA) target to perform polymerase chain reaction (PCR). The systems can be cartridge-based systems (also "cartridges" or "cartridge-based thermocyclers" herein) that enable low-cost, disposable PCR systems to be realized. In some cases, the cartridges can be real-time, multiplexed systems (also "multiplexed assays" herein). The cartridges can be coupled to other PCR system components, such as, for example, one or more other cartridges and/or an instrument. In some implementations, PCR systems comprising disposable cartridge system(s) coupled with a durable instrument can be provided.

The cartridges can be configured to move fluid between distinct chambers. Each chamber can have a given temperature, composition, volume and/or shape. Individual chambers can be heated, cooled, and/or compressed to mix fluid within the chamber or to propel fluid in the chamber into another chamber. Further, the chambers can be shaped to inhibit trapping of air bubbles. The chambers can be configured to allow rapid thermal equilibration. The chambers have any shape that does not interfere with the movement of fluid between chambers, which includes generally planar or bubble-like shapes, including hemispherical and spherical shapes.

Reference will now be made to the figures, wherein like numerals refer to like parts throughout. It will be appreciated that the figures (and features therein) are not necessarily drawn to scale.

FIG. 1 shows a single unit thermocycler (also "thermocycling unit" herein). The thermocycler can rapidly change the bulk temperature of a small volume of fluid between a first temperature $T_1$ and a second temperature $T_2$. In some cases, $T_1 < T_2$; for example, $T_1$ can be nominally about 55° C., about 60° C., about 65° C., or any temperature between about 55° C. and about 65° C., and $T_2$ can be nominally about 95° C. In some examples, $T_1$ can be about 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C. and the like. Any description herein in relation to a given value of $T_1$ equally applies to other values of $T_1$ at least in some configurations. In some examples, $T_2$ can be about 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C. and the like. Any description herein in relation to a given value of $T_2$ equally applies to other values of $T_2$ at least in some configurations.

The thermocycler can comprise one or more parts. In some examples, the thermocycler can comprise a disposable portion 1 and a durable or reusable portion 2. The disposable portion (also "disposable" herein) can be provided, for example, on a single cartridge or cartridge portion, or on (e.g., spread across) multiple cartridges or cartridge portions. In one embodiment, the durable portion of a thermocycler comprises a receptacle or attachment means for receiving the disposable portion. In one example, the components of the disposable portion shown 1 are provided on a single cartridge. In one embodiment, this cartridge couples to another cartridge. In a further embodiment, this cartridge couples with an instrument or analyzer. In some cases, the disposable is used once and disposed of. For example, all parts of the disposable are discarded. The durable or reusable portion can be provided, for example, on a durable instrument or analyzer. In some cases, the durable instrument and at least a subset or all parts associated with can be reused through the life of the instrument. In one embodiment, for simultaneous thermocycling of a plurality of samples, a plurality of cartridges are used simultaneously with one reusable portion or instrument. For example, the multiple cartridges are aligned in parallel.

In an example, the disposable comprises of a polydimethylsiloxane (PDMS) top block 3 which has cavities molded within it. Two shallow chambers, left chamber 4 (e.g., at the first temperature $T_1$) and right chamber 5 (e.g., at the second temperature $T_2$), can be provided. Each chamber can have nominal dimensions of about 12 mm in diameter and about 0.5 mm in height. The chambers can be connected by a connecting channel 6 with a length of about 5 mm and a cross-section with a height of about 0.30 mm and a width of about 0.50 mm. The areas above the chambers can be compliant and can be deformed such that the internal volume of the chamber can be changed to as little as, for example, 10% of its original undeformed volume of $\pi \times (12 \text{ mm})^2/4 \times (0.5 \text{ mm})$ or about 56 microliters (μL).

In some examples, cartridges of the disclosure can comprise chambers that are configured to be deformed on one side (e.g., along a top surface of each chamber) or on two sides (e.g., along a top and a bottom surface of each chamber). In some cases, individual chambers can be deformed using different configurations. In some examples, the deformation can result in a change of internal volume of the chamber to less than about 90% of its original undeformed volume, less than about 80% of its original undeformed volume, less than about 70% of its original undeformed volume, less than about 60% of its original undeformed volume, less than about 50% of its original undeformed volume, less than about 40% of its original undeformed volume, less than about 30% of its original undeformed volume, less than about 20% of its original undeformed volume, less than about 10% of its original undeformed volume, and the like.

In various implementations, the boundaries of the chambers and/or the channels connecting said chambers are defined by any sealing means or barrier which closes a chamber to prevent movement of fluid into or out of the chamber. In one embodiment, any chamber or component of a thermocycler comprises one or more openings with sealing means to allow for the addition or removal of gases, solids and/or fluids, e.g., an inlet or port. In one example, an opening comprises a seal or valve. In one embodiment, a chamber and/or channel is opened by an external force applied to or next to the chamber and/or channel. In one example, the seal is a burstable seal. Methods to open a seal include, without limitation, application of pressure, mechanical actuation, heat and chemical reaction. Barriers include those which are fixed, movable or alterable components inserted into channels of the cartridge. Barriers and seals are alternatively a component of a durable portion of a thermocycling unit. In one embodiment, barriers are an external force provided by the durable portion of a thermocycling unit, for example, a clamp. In one embodiment, some of the channels remain open during a thermocycling reaction, while others may remain closed. In one example, a channel and/or chamber is opened or closed at any time point prior to or during a thermocycling reaction. Once a barrier or seal is opened, a substance, such as a fluid, in many implementations, is moved from one chamber to another, for example, by pressure from an actuator.

In some implementations, channels 7 and 8 can allow filling and extracting of fluid (e.g., sample) from the chambers 4 and 5, respectively, via a filling or collecting device (e.g., a syringe, or ancillary chambers on the same disposable). The channels can have a cross-section with a height of about 0.3 mm and a width of about 0.5 mm. A plate 9 (e.g., a thin plate of glass or some other suitable material) can be bonded to the PDMS top block (e.g., using a plasma cleaning process). The bonding can allow very high adhesion between the two materials to support large internal pressures caused by vapor pressure and compression of the chamber volumes. The plate 9 can have a thickness of, for example, about 0.14 mm.

The durable instrument 2 can interact with the disposable 1. The parts or components of the durable instrument 2 that interact with the disposable 1 can include, for example, actuator heads 10 and 11. The actuator heads can deform the fluidic chambers to move fluid from one chamber (e.g., the chamber held at $T_1$) to the other chamber (e.g., the chamber held at $T_2$), or vice versa, over multiple cycles (e.g., between 20 and 30).

In some implementations, the plate 9 can be supported and in contact with heater blocks 12 and 13. The heater blocks can be formed of a heat conductive material such as, for example, aluminum, copper or other metals. The heater blocks can be kept at temperatures $T_1$ and $T_2$ by heaters 14 and 15, respectively. In some cases, the heaters 14 and 15 can be thin film resistive heaters with leads 16 and 17, respectively, for providing current to each heater. In other cases, the heater blocks can be heated by other heaters 14, 15, such as, for example, thermoelectric heaters, thin film heaters, etc. The two heater blocks can be separated by an air gap to minimize temperature coupling between the two chambers. Temperature probes 18 and 19 (e.g., thermocouples) can be used to monitor the heater block temperatures. In an additional embodiment, a means for measuring temperature, e.g., temperature probe, is coupled to or in contact with one or more regions of the disposable, for example, one or more chambers. The temperature probes can be used in a temperature control feedback loop to keep the temperatures constant at their respective set-points (e.g., $T_1$ and $T_2$). In one embodiment, he control feedback loop is provided on the durable instrument. For example, the thermocouple signals can be acquired by a data acquisition board and further processed on a processing or computing unit of the durable instrument. Based on the temperature reading received and/or other control parameters (e.g., temperature programming, optical detection signal of reaction progress etc.), the durable instrument provide control signals to one or more components (e.g., heater voltage or current controls, actuators, etc.) in a feedback mechanism.

In yet other cases, heater blocks are not be used; instead, heating can be provided directly to the chambers (or to a structure surrounding the chambers, such as, for example, the plate 9 and/or the top block 3, or a laminate layer on a laminated cartridge described elsewhere herein). For example, convective heating (or cooling) using phase change or a fluid such as oil, air or water can be used instead. Any description herein of heating of chambers equally applies to cooling of chambers at least in some configurations.

In one embodiment, one or more heaters are warmed up (or alternatively cooled down) to a desired reaction temperature prior to performing a thermocycling reaction. In another embodiment, one or more heaters are warmed up (or alternatively cooled down) during the course of a thermocycling reaction. In one example, a heater is warmed up to a desired temperature in less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, less than about 1 minute, or less than about 30 seconds.

In some embodiments, the durable portion of a thermocycler provided herein comprises a plurality of heaters, wherein each heater provides temperature control for one or more chambers of a cartridge. For example, the thermocycler comprises 1, 2, 3, 4 or more heaters. In another embodiment, the thermocycler comprises one or more cooling elements. In one embodiment, a thermocycler comprises two heaters which provide temperature control for one chamber of a cartridge, for example, the cartridge is disposed between the two heaters. In another example, one or more heaters provide temperature control to one or more cartridges simultaneously, wherein the cartridges are aligned in parallel.

Figure 2A:
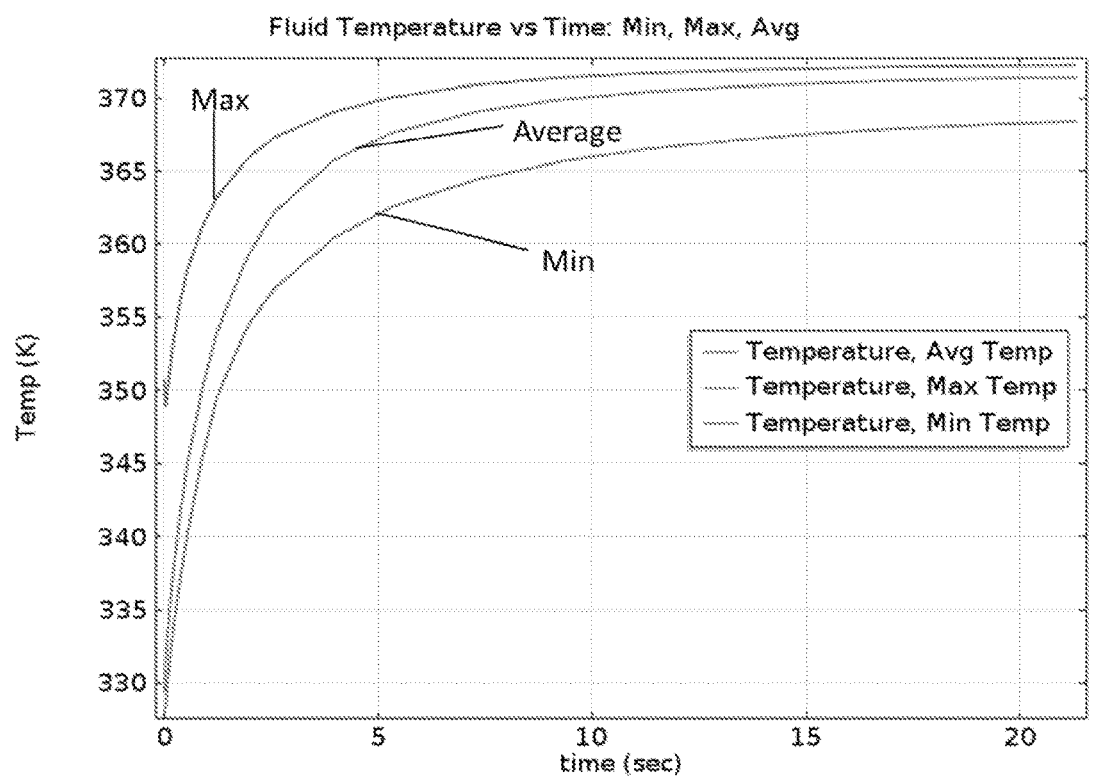
FIG. 2A shows temperature of fluid in right chamber (hot) immediately after fluid transfer from left chamber (cold). The time to achieve the hot average temperature is only about 5 seconds. The temperature is expressed in degrees Kelvin (K).

FIG. 2A shows a simulated profile of fluid temperature in a hot chamber (e.g., right chamber 5) immediately after fluid transfer from a cold chamber (e.g., left chamber 4). The fluid in the cold chamber is initially held at a temperature $T_1$ and is moved into the hot chamber at time t=0. The fluid immediately increases in temperature and at about 5 seconds the average temperature is at $T_2 \pm 3°$ C. In this example, $T_1$ is approximately 55° C. (328 K) and $T_2$ is approximately 95° C. (368 K).

Figure 2B:
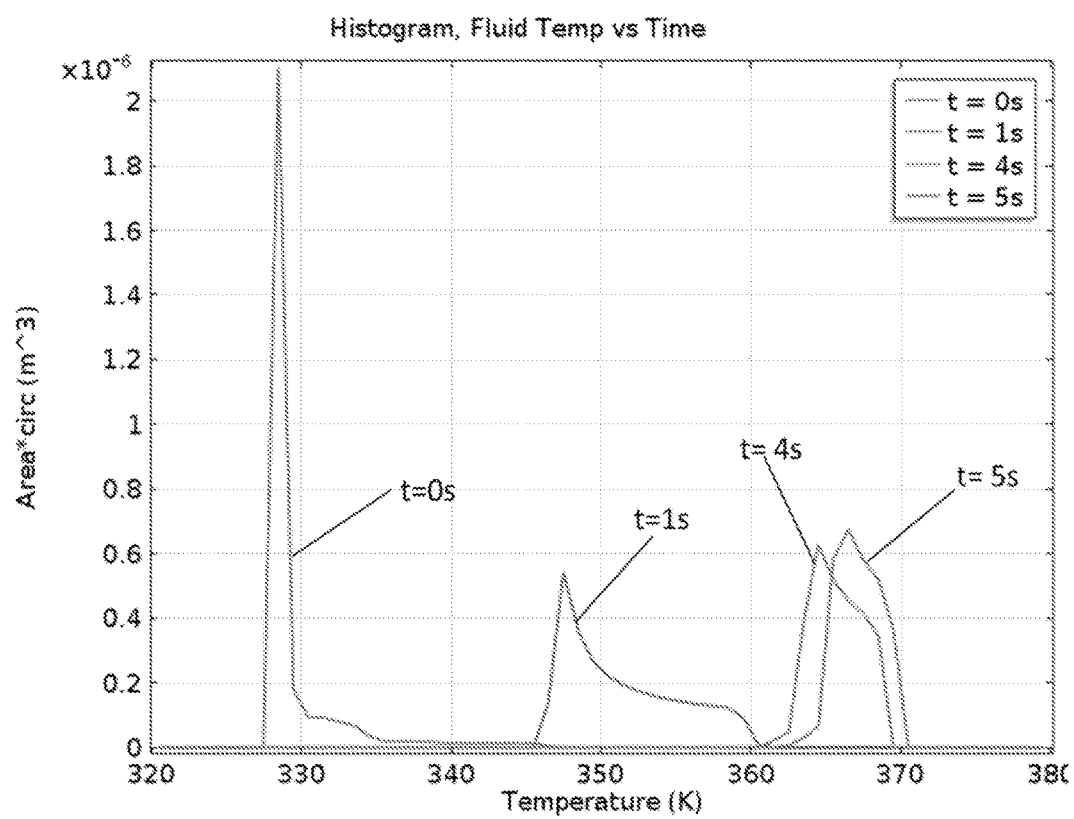
FIG. 2B shows a histogram of temperatures of the fluid entering the hot chamber in FIG. 2A. Most of the fluid is at the hot temperature±3° C. (3 K) in about 5 seconds. The temperature is expressed in degrees Kelvin (K).

FIG. 2B shows a histogram of temperatures of the fluid entering the hot chamber in FIG. 2A with a progression from an average of 55° C. (328 K) to an average of 95° C. (368 K) in about 5 seconds. In this example, most of the fluid volume reached a temperature within a band of 95° C. (368 K)±3° C. within only about 5 seconds.

In various embodiments, the cartridges of the disclosure allow very short dwell times for each thermal cycle to be achieved. This can be an important factor in establishing a fast time-to-result PCR test. The timescales of molecular biological reactions associated with PCR can be much shorter than 1 second. Therefore, the time-determining factor in rapid thermocycling can be the length of dwell time for each thermal cycle. In this example, for 20 cycles at about 5 second dwell times in each chamber (cycle time of about 10 seconds), the total thermocycling time can be about 200 seconds (3.3 minutes). Most commercial thermocyclers (e.g., ABI 7900) require 30 minutes to an hour to run this PCR because of the length of time needed to heat and cool the thermal mass of these systems (e.g., disposable tubes and/or plates held in metal blocks). Thus, PCR with a given PCR efficiency (e.g., 92% PCR efficiency) can be completed within a total thermocycling time that is at least 9 times (e.g., 30×60 seconds/200 seconds=9) shorter than the corresponding thermocycling time on a conventional system. In another example, a Roche LightCycler II 480 Real Time PCR System can require about 23 minutes to complete 20 cycles, while a cartridge with two-sided heating and dwell times of about 3 seconds, described in greater detail elsewhere herein, can perform this PCR in about 2 minutes (e.g., 20×3 seconds×2=120 seconds=2 minutes), or about 11.5 faster (e.g., 23 minutes/2 minutes=11.5). In some examples, cartridges of the disclosure can complete a PCR with a given PCR efficiency within a total thermocycling time that is shorter than the corresponding (e.g., having the same PCR efficiency) thermocycling time on a conventional system by a factor of at least about 5, at least about 6, at least about 7, at least about 8, at least about 9, at least about 9.5, at least about 10, at least about 10.5, at least about 11, at least about 11.5, at least about 12, at least about 12.5, at least about 13, at least about 14, at least about 15, or more. In some examples, the PCR efficiency can be at least about 84%, 86%, 88%, 90%, 91%, 92%, 93%, 94%, 95%, and the like. In an example, PCR with a PCR efficiency of at least 92% is completed within a total thermocycling time that is at least about 9 times shorter than the thermocycling time on a conventional system with the same PCR efficiency. In another example, PCR with a PCR efficiency of at least 92% is completed within a total thermocycling time that is at least about 11.5 times shorter than the thermocycling time on a conventional system with the same PCR efficiency.

In some examples, the total thermocycling time can be less than about 10 minutes, less than about 8 minutes, less than about 6 minutes, less than about 5 minutes, less than about 4 minutes, less than about 3 minutes, less than about 2 minutes, less than about 1 minute, less than about 0.5 minute, and the like. In some examples, a cartridge-based thermocycler has a total thermocycling time of about 5 minutes, about 4 minutes, about 3 minutes, about 2 minutes, about 1 minute, about 0.5 minute, or less. In other examples, the total thermocycling time to achieve a PCR efficiency of at least 85% is less than about 15 minutes, less than about 10 minutes, less than about 9 minutes, less than about 8 minutes, less than about 6 minutes, less than about 5 minutes, less than about 4 minutes, less than about 3 minutes, less than about 2 minutes, less than about 1 minute, less than about 0.5 minute, and the like. In other examples, the total thermocycling time to achieve a PCR efficiency of at least 90% is less than about 15 minutes, less than about 10 minutes, less than about 9 minutes, less than about 8 minutes, less than about 6 minutes, less than about 5 minutes, less than about 4 minutes, less than about 3 minutes, less than about 2 minutes, less than about 1 minute, less than about 0.5 minute, and the like. In other examples, the total thermocycling time to achieve a PCR efficiency of at least 91% is less than about 15 minutes, less than about 10 minutes, less than about 9 minutes, less than about 8 minutes, less than about 6 minutes, less than about 5 minutes, less than about 4 minutes, less than about 3 minutes, less than about 2 minutes, less than about 1 minute, less than about 0.5 minute, and the like. In other examples, the total thermocycling time to achieve a PCR efficiency of at least 92% is less than about 15 minutes, less than about 10 minutes, less than about 9 minutes, less than about 8 minutes, less than about 6 minutes, less than about 5 minutes, less than about 4 minutes, less than about 3 minutes, less than about 2 minutes, less than about 1 minute, less than about 0.5 minute, and the like. In other examples, the total thermocycling time to achieve a PCR efficiency of at least 95% is less than about 15 minutes, less than about 10 minutes, less than about 9 minutes, less than about 8 minutes, less than about 6 minutes, less than about 5 minutes, less than about 4 minutes, less than about 3 minutes, less than about 2 minutes, less than about 1 minute, less than about 0.5 minute, and the like.

The cartridges of the present disclosure can be used as multiplexed assays. In one aspect, a thermocycling unit provided herein comprises or is operably connected to a detector. For example, one or more components of a cartridge are configured to enable detection of a sample within the component. For example, the detector detects the existence of an analyte in the sample or the amount of a signal indicative of a characteristic of the sample. Signals include, without limitation, luminescence, fluorescence, turbidity, radioactivity and electrical currents. In an exemplary embodiment, a nucleic acid analyte is detected using a detectable label. Exemplary labels include, without limitation, radiolabels, intercalating dyes, enzymes, haptens, chemiluminescent molecules, and fluorescent molecules. In some implementations, one or more regions of the cartridge (e.g., one or more of the chambers, a region in the fluid flow path between chambers, etc.) can be monitored to detect amplification of the target DNA (e.g., using optical or other detection methods, such as bioimpedance and colorimetry). In some cases, the detection can be implemented through optical multiplexing by using one or more fluorescent probes. In one example, each target DNA sequence can be detected by a fluorescent label (also "fluorophore" herein), with a different label corresponding to each target. In another example, multiple labels can be applied to each target DNA sequence. The detection can be performed in real-time. For example, multiplexed real-time PCR can be used to identify the presence and/or the quantity of particular sequences of DNA.

Further, the thermocycling unit can be reproduced multiple times on a more complicated cartridge (e.g., a disposable cartridge) or cassette. For example, multiple thermocycling units can be deployed within a cartridge to perform a multiplexed assay. In some cases, at least a subset or all of the thermocycling units can be identical. In other cases, one or more of the thermocycling units can be unique (e.g., each thermocycling unit can have a different configuration including, but not limited to, chamber shape, volume, temperature etc.). In some implementations, one or more of the thermocycling units can have a dedicated detector. For example, each of the thermocycling units can have a dedicated detector. Alternatively, at least a subset of the thermocycling units can share a detector. For example, each thermocycling unit can have a switching element in front of a time multiplexed detector. Individual detectors can be suitable or configured for detecting PCR on one or more of the thermocycling units.

The cartridges of the present disclosure can comprise additional cartridge portions or be coupled to one or more other cartridges. For example, individual thermocycling units can be linked to one or more reaction chambers (e.g., on the additional cartridge portion or on another cartridge) for implementing sample preparation. In some cases, multiple thermocycling units can be linked to a single set of reaction chambers for implementing sample preparation. In other cases, multiple thermocycling units can be linked to multiple sets of reaction chambers for implementing sample preparation. In an example, a first subset of thermocycling units can be linked or connected to a first set of reaction chambers while a second subset of thermocycling units can be linked or connected to a second set of reaction chambers. In another example, one or more individual thermocycling units can each be linked to its own set of reaction chambers.

Each set of reaction chambers can include, for example, 1, 2, 3, 4, 6, 8, 10 or more reaction chambers.

Starting volume (also "sample starting volume" or "sample volume" herein) can be important in PCR (e.g., for high sensitivity PCR reactions). At low target analyte concentration, a larger sample volume can facilitate detection by increasing probability of the analyte being present in the sample for PCR analysis. Because of sample composition variability (e.g., in real human samples such as urine or saliva), the sample can be processed through a pre-filter to remove, for example, solid matter (e.g., insoluble material) prior to a purification step. In one aspect, the cartridges provided herein comprise or are coupled to a chamber or vessel for sample preparation. In one example, the sample is processed prior to addition to a cartridge or processed, in whole or in part, in one or more chambers or components of a cartridge. A first step in purification can be to lyse all the organisms of interest (e.g., bacteria, viruses, etc.) to release total nucleic acid. A next step in purification can involve a solid phase material (e.g., filter or beads) with an affinity for the nucleic acid or molecule of interest. After affinity capture of the nucleic acid to the solid phase material, the nucleic acid can be washed with a wash solution prior to elution with water. The elution can contain the purified nucleic acid to be used for PCR analysis. Using as much of the elution as possible for PCR can be desirable in order to increase or maximize the sensitivity. For example, a PCR starting volume of more than about 25 µL (e.g., 50 µL) can be used to achieve improved sensitivity. This can allow the PCR to proceed with low target concentrations (e.g., 10 copies/µL). Therefore, rapid thermocyclers of the disclosure can be configured to provide an increased heat transfer rate (° C./second) while ensuring that this heat transfer rate can be achieved with a reasonable starting volume. In one embodiment, a sample preparation chamber or vessel comprises, or is connected to an auxiliary chamber which comprises, sample preparation reagents such as Lysozyme or Proteinase K. In one embodiment, a sample preparation chamber or vessel comprises, or is connected to an auxiliary chamber which comprises, a solid support for immobilizing an analyte, e.g., nucleic acid, in the sample. Solid supports include magnetic supports, such as beads, that can be manipulated by a magnetic field. In another embodiment, a sample preparation chamber or vessel is connected, directly or indirectly, to a waste chamber for collecting sample material which interferes with an amplification reaction (e.g., cell pellet).

A cartridge-based thermocycler of the present disclosure can have any suitable starting volume, such as at least about 25 µL, at least about 30 µL, at least about 35 µL, at least about 40 µL, at least about 45 µL, at least about 50 µL, at least about 55 µL, at least about 60 µL, at least about 65 µL, at least about 70 µL, at least about 75 µL, at least about 80 µL, at least about 85 µL, at least about 90 µL, at least about 95 µL, at least about 100 µL, and the like. In some examples, a cartridge-based thermocycler has a starting volume of about 25 µL, 30 µL, 35 µL, 40 µL, 45 µL, 50 µL, 55 µL, 60 µL, 65 µL, 70 µL, 75 µL, 80 µL, 85 µL, 90 µL, 95 µL, 100 µL or more. In one embodiment, one or more chambers of a cartridge has a non-compressed volume capacity of at least about 10 µL, at least about 15 µL, at least about 25 µL, at least about 30 µL, at least about 35 µL, at least about 40 µL, at least about 45 µL, at least about 50 µL, at least about 55 µL, at least about 60 µL, at least about 65 µL, at least about 70 µL, at least about 75 µL, at least about 80 µL, at least about 85 µL, at least about 90 µL, at least about 95 µL, at least about 100 µL, and the like. In another embodiment, one or more chambers of a cartridge has a non-compressed volume capacity of at least about 50 µL, at least about 100 µL, at least about 150 µL, at least about 200 µL, at least about 250 µL, at least about 500 µL, and the like. In one embodiment, one or more chambers of a cartridge has a compressed volume of less than about 100 µL, less than about 50 µL, less than about 40 µL, less than about 30 µL, less than about 20 µL, less than about 10 µL, or less than about 5 µL. The connecting channel disposed between two chambers has a volume, for example, of about 1%, 2%, 3%, 4%, 5%, 6%, 7%, 8%, 9%, 10% or 20% of the total fluid volume of the two chambers. For example, from about 1 µL to about 50 µL.

A cartridge-based thermocycler of the present disclosure can have a product rate of at least about 10 µL° C./second, at least about 25 µL° C./second, at least about 50 µL° C./second, at least about 75 µL° C./second, at least about 100 µL° C./second, at least about 150 µL° C./second, at least about 200 µL° C./second, at least about 250 µL° C./second, at least about 300 µL° C./second, at least about 325 µL° C./second, at least about 350 µL° C./second, at least about 375 µL° C./second, at least about 400 µL° C./second, at least about 425 µL° C./second, at least about 450 µL° C./second, at least about 500 µL° C./second, at least about 550 µL° C./second, at least about 600 µL° C./second, at least about 650 µL° C./second, at least about 700 µL° C./second, and the like. In some examples, a cartridge-based thermocycler has a product rate of about 10 µL° C./second, about 25 µL° C./second, about 50 µL° C./second, about 75 µL° C./second, about 100 µL° C./second, about 150 µL° C./second, about 200 µL° C./second, about 250 µL° C./second, about 300 µL° C./second, about 325 µL° C./second, about 350 µL° C./second, about 375 µL° C./second, about 400 µL° C./second, about 425 µL° C./second, about 450 µL° C./second, about 500 µL° C./second, about 550 µL° C./second, about 600 µL° C./second, about 650 µL° C./second, about 700 µL° C./second, or more. In one example, a starting volume of 50 µL with a heating or cooling rate of about 35° C. in 5 seconds is used. In this example, a product rate of about 350 µL° C./second is achieved. In some examples, a cartridge-based thermocycler can have a product rate within a range of about 10-700 µL° C./second, about 25-700 µL° C./second, about 100-700 µL° C./second, about 10-450 µL° C./second, about 25-450 µL° C./second, about 100-450 µL° C./second, about 300-400 µL° C./second, and the like. In some examples, a cartridge-based thermocycler can have a product rate within a sub-range. For example, the sub-range can be about (or at least about): 10%, 20%, 30%, 40%, 50%, 60%, 70%, 80%, 90%, 95%, or more of a range (e.g., a range of about 10-700 µL° C./second, about 25-700 µL° C./second, about 100-700 µL° C./second, about 10-450 µL° C./second, about 25-450 µL° C./second, about 100-450 µL° C./second, about 300-400 µL° C./second, and the like). In some cases, the sub-range can comprise a lower portion of a range, an upper portion of a range, or an interior portion of a range. In some cases, the sub-range can have a width of at least about 0.01 µL° C./second, at least about 0.1 µL° C./second, at least about 1 µL° C./second, at least about 24° C./second, at least about 5 µL° C./second, at least about 10 µL° C./second, at least about 20 µL° C./second, at least about 50 µL° C./second, at least about 100 µL° C./second, at least about 150 µL° C./second, at least about 200 µL° C./second, at least about 250 µL° C./second, and the like.

A cartridge-based thermocycler having a suitable starting volume can have a cycle time of less than about 20 seconds, less than about 15 seconds, less than about 12 seconds, less than about 11 seconds, less than about 10 seconds, less than about 9 seconds, less than about 8 seconds, less than about 7 seconds, less than about 6 seconds, less than about 5 seconds, less than about 4 seconds, and the like. In some examples, a cartridge-based thermocycler has a cycle time of about 12 seconds, about 11 seconds, about 10 seconds, about 9 seconds, about 8 seconds, about 7 seconds, about 6 seconds, about 5 seconds, about 4 seconds, or less.

The PCR chambers 4 and 5 can be coupled to one or more other chambers in some implementations. In an example, the disposable cartridge can be formed with three chambers. An additional or auxiliary chamber (not shown) can have nominal dimensions of about 12 mm in diameter and about 0.5 mm in height. In some examples, the auxiliary chamber can be a pre-chamber connected, permanently or temporarily (e.g., before being sealed off), to one or more PCR chambers of the disclosure. The auxiliary chamber can be capped by a thin flexible membrane material. The auxiliary chamber (also "blistered" chamber herein) can contain lyophilized reagents of Lysozyme and Proteinase-K stored in dry (e.g., powder) form. The auxiliary chamber may or may not be heated (e.g., by a heater on the durable instrument). In one example, a heater on a surface of the auxiliary chamber (e.g., on a back side of the auxiliary chamber) can apply heating needed for heat activation in the auxiliary chamber. The membrane can be blistered into the volume of the auxiliary chamber to move fluid to the next series of chambers representing the PCR thermocycling stage (e.g., chambers 4 and 5). The blistering can be done, for example, by an external actuator (e.g., an actuator on the durable instrument). In some cases, the actuator can execute minute movements (e.g., movements of about 0.1 mm) to mix the contents of the auxiliary chamber. The auxiliary chamber can be compressed by an actuator to move fluids to downstream processes. For example, the contents of the auxiliary chamber can be pushed out by the actuator deforming the blisterable membrane into the hot chamber (e.g., chamber 5) in the thermocycling stage. In some examples, the cartridge can comprise a valve that seals the contents (e.g., the sample fluid) in the hot thermocycling chamber. In one embodiment, the blistered chamber comprises reagents useful for performing a nucleic acid-based amplification reaction and/or detection of nucleic acid amplification products. Exemplary reagents include, without limitation, a hybridization oligonucleotide (e.g., probe, primers), ions and buffers. In one example, the blistered chamber comprises reagents for sample preparation. In another example, the blistered chamber comprises lyophilized or otherwise dried reagents.

In some examples, the contents can be sealed in the thermocycling chambers (e.g., chambers 4 and 5) via one or more pinch or clamp points, described in greater detail elsewhere herein. The pinch points can be pinched by, for example, one or more components (e.g., actuators or pistons) on the durable instrument. The pinch points can be clamped. In some cases, one or more valves are used (e.g., to control fluid and/or gas flow, such as to close and/or open channels to chambers). In some cases, the valve can be used instead of the pinch point. In some cases, the valve can be used in combination with the pinch point. In some cases, one or more valves can be combined with one or more pinch points.

The hot (thermocycling) chamber can be heated (e.g., maintained at about 95° C.) by an external thin film heater. Upon receiving the sample fluid from the auxiliary chamber, the contents of the hot chamber can be elevated in temperature for a given period of time (e.g., 95° C. for about 1 minute). This can inactivate the Proteinase-K and further lyse the cell walls of bacteria not lysed by the Lysozyme, thereby releasing DNA sample in the sample fluid from cell nuclei and disabling inhibitory factors to PCR. An actuator can be used to compress the hot chamber to move or push the sample fluid (e.g., contents of chamber 5) to the cold chamber (e.g., chamber 4) in the thermocycling stage.

The cold (thermocycling) chamber may or may not be heated (e.g., maintained at about 65° C.). Lyophilized "Master Mix" reagents including primers and TaqMan® probes can be stored in the cold chamber (e.g., maintained at about 65° C.). After mixing with the Master Mix, the sample fluid can be ready for thermocycling. An actuator can be used to compress the cold chamber to move or push the sample fluid back to the hot chamber to begin the thermocycling processes of the disclosure.

Thus, cartridge-based rapid thermocyclers having one or more auxiliary chambers can be provided. The auxiliary chambers can be used, for example, for filling, emptying or regulation of sample fluid in the PCR chambers. In an example, an auxiliary chamber can be used for pre-PCR preparation of the sample.

Laminated Disposable Cartridge

In some implementations, the cartridge comprising the chambers can have a laminate construction. The laminated cartridge can be disposable. For example, the laminated cartridge can be provided as a disposable element of a low-cost PCR system. In some cases, the laminated cartridge can be used strictly for PCR without addressing pre-PCR preparation of the sample. Alternatively, at least a portion of pre-PCR preparation can be provided on the laminated cartridge. Cartridges of the disclosure, including laminated cartridges, can be used in concert with mechanical actuation for moving a fluid from one chamber to another. The fluid in each chamber can be rapidly brought to desired temperatures for PCR (e.g., within 5 seconds). In some examples, each chamber can be held at a given PCR temperature (e.g., 95° C. or 65° C.) using fixed-temperature heater blocks. Other examples of heating configurations are described in greater detail elsewhere herein. Further, the cartridges enable the fluid sample to be optically interrogated for a fluorescence signal. Low-cost, disposable materials can be used to construct robust cartridges that can resist high pressures of PCR. Any aspects of the disclosure described in relation to laminated cartridges equally applies to other cartridges of the disclosure at least in some configurations.

Figure 3:
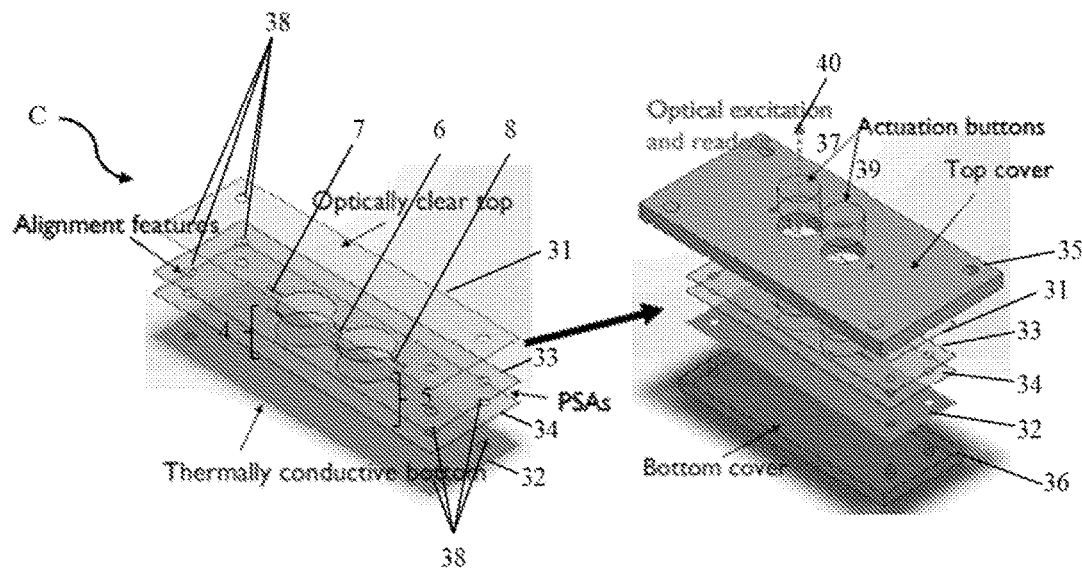
FIG. 3 shows a layered cartridge without separate optical window. Readout is directly in one of the wells.

FIG. 3 provides an example of a laminated cartridge C comprising layered sheets or membranes 31 and 32 (e.g., formed from plastic or another suitable material) and pressure sensitive adhesive (PSA), collectively referred to as laminate layers herein. The PSA can be provided as layers 33 and 34 (also "PSAs" herein) between the layered sheets of plastic 31 and 33. The PSA can be used to bond two outer membranes (e.g., plastic membranes) together. Other examples of techniques that can be used to bond laminate layers include use of other adhesives (e.g., liquid or solid adhesives), fusing the laminate layers together through (e.g., heat, ultrasound), etc.

The PSA layers can each have a given thickness. The thickness of the PSAs (e.g., combined thickness of the PSA layers) can define internal volumes of the PCR chambers 4 and 5. For example, the membranes 31 and 32 can form upper and lower surfaces, respectively, of each chamber, and the PSAs can form side walls of each chamber having a height corresponding to the combined thickness of the PSAs. In some cases, additional layered sheets (e.g., plastic layers) can be provided in combination with the PSAs. For example, additional plastic layers can be added to increase the fluid holding volumes of the chambers. In some cases, the volumes of the chambers can be identical. In other cases, the volumes of the chambers can differ.

The laminated cartridge can be heated on one or more surfaces. For example, at least one of the membranes 31, 32 (e.g., bottom membrane 32) can be positioned adjacent to heaters or adjacent to heater blocks (not shown) and formed of a thermally conductive material (e.g., polyimide, or polyester) configured for efficient heat transfer such that fluid that enters each chamber is rapidly equilibrated at a desired temperature.

Figure 4:
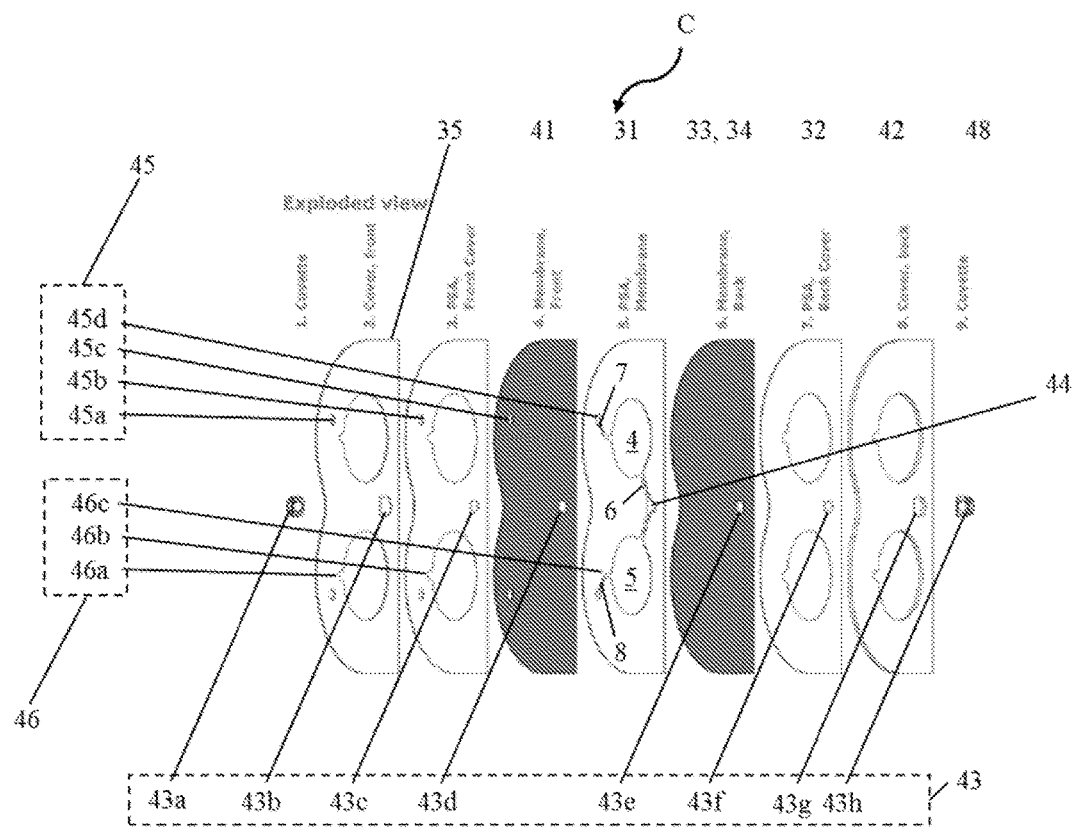
FIG. 4 is an exploded view of separate layers of a layered cartridge that includes an embedded optical window.
Figure 5:
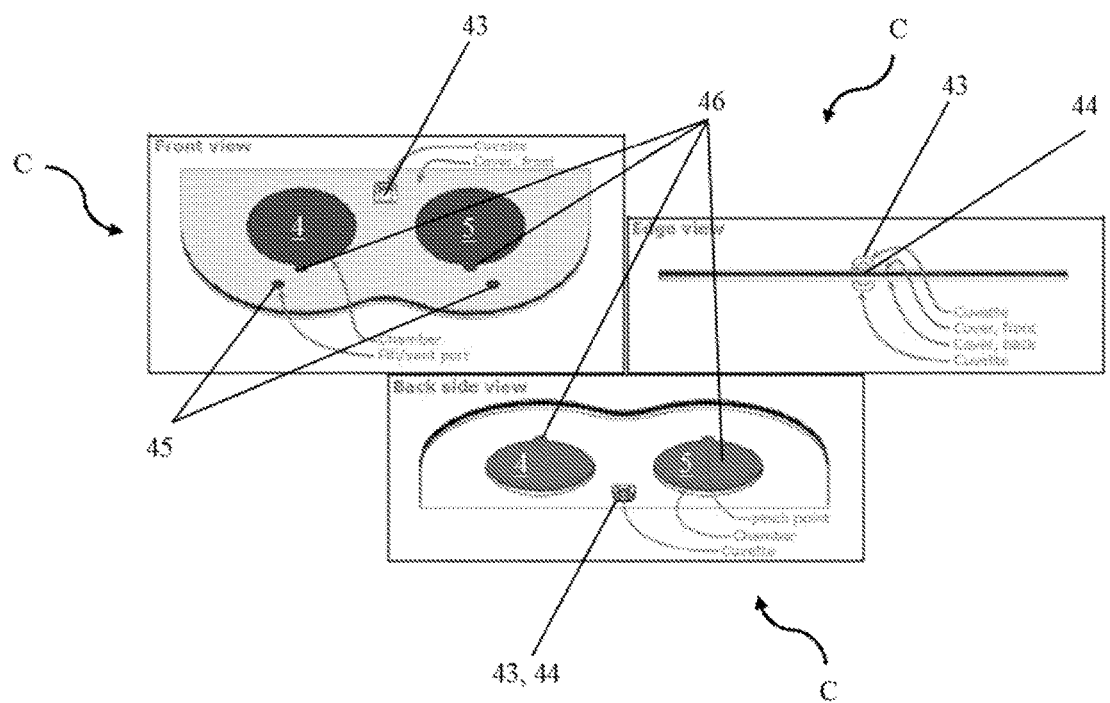
FIG. 5 shows front, back and side views of an assembled laminated cartridge with optical window embedded.
Figure 6:
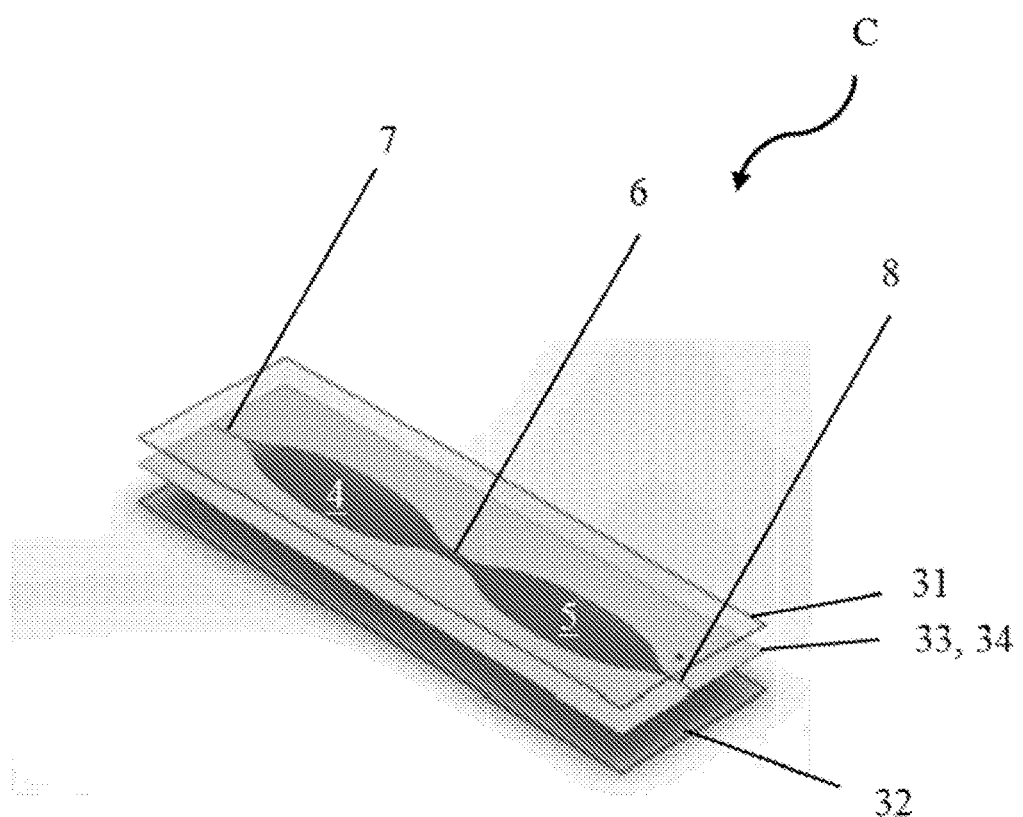
FIG. 6 is an exploded view of a three-layer "blister pack" disposable.

The device geometry can be configured for efficient heat transfer and cost by changing thicknesses of the layered sheets or membranes 31 and 32 (e.g., thicknesses of the plastic). For example, a thinner plastic layer which is less durable provides improved heat transfer rates to the chambers. Further, the device geometry can be configured for efficient heat transfer and cost by changing heights and diameters of the PCR chambers. As described above, heights of the PCR chambers can be changed, for example, by changing the number and thickness of individual laminate layers that make up the sides of each chamber. The diameters of the PCR chambers can be changed by, for example, providing PSA layers with cutouts of different diameters. In one example, as shown in FIG. 3, the cutouts can be substantially circular. In another example, as shown in FIGS. 4, 5 and 6, the cutouts can be substantially oval. In some cases, the cutouts and resulting chambers can be shaped (e.g., in a tear drop shape) in order to decrease trapping of air or vapor bubbles in the fluid being cycled on the cartridge. In some cases, chambers and/or fluid flow paths can be shaped (e.g., in a tear drop shape) to avoid or reduce re-entrant or sharp corners and/or steps that can serve as nucleation sites during filling and/or cycling of fluid on the cartridge. In an example, the chambers and/or fluid flow paths can be configured such that their surface maintains a curvature that is larger than a curvature of the wavefront of the fluid flowing across the surface. Further, the cutouts can include various features, such as the connecting channel 6 and the channels 7 and 8 for filling/extracting fluid (e.g., sample) to/from the chambers 4 and 5. In some cases, the channels 7 and 8 can be used for filling, extracting and/or venting. For example, channel 7 is useful as a filling channel for filling (e.g., of fluid) and channel 8 is useful as a venting channel for venting (e.g., to prevent gases from being trapped in the device while filling), and vice versa. In one embodiment, the channel that is used for venting connects the respective chamber 5 to outside air. For example, the channel 8 can connect the chamber 5 to the ambient environment. As described elsewhere herein, fill or vent ports (e.g., ports 45 in FIG. 4), can be used for connecting to the channels 7 and/or 8. In some cases, a fill port can be used for extraction of fluid. Fill/extraction ports and vent ports may or may not have the same configuration. In an example, the port exposed to the surroundings (e.g., outside air) has a gas permeable seal (not shown) to allow air in but to keep the device from being contaminated. In another example, the port exposed to the surroundings can comprise a check valve for letting gas out from the chamber (e.g., via the channel) while not allowing air or other contaminants into the chamber. After filling and/or venting, each channel can be closed to encapsulate the fluid during thermocycling.

In some implementations, one or more of the materials comprising the laminate layers of the cartridge can have hydrophilic properties. For example, plastic materials (e.g., plastic used to form one or more of the membranes) can have hydrophilic properties. The hydrophilic nature of the materials can provide various advantages for cartridge operation. For example, cartridge chambers (and/or fluid flow paths) having hydrophilic surfaces can be filled without leaving behind small trapped air or vapor bubbles. Such bubbles can become nucleation sites for larger air or vapor bubbles as the cartridge is heated for PCR. In some cases, this can lead to lower PCR efficiency. In some cases, the amount of air or vapor bubbles trapped during filling can be decreased by using cartridges with chambers (and/or fluid flow paths) having hydrophilic properties. Further, bubble formation can cause signal dropouts during in the detection system (e.g., during optical detection). Hydrophilic properties can be used in concert with the previously described shaped chambers and/or shaped fluid flow paths to achieve desired fluid flow conditions during filling and cycling on the cartridge.

Figure 13:
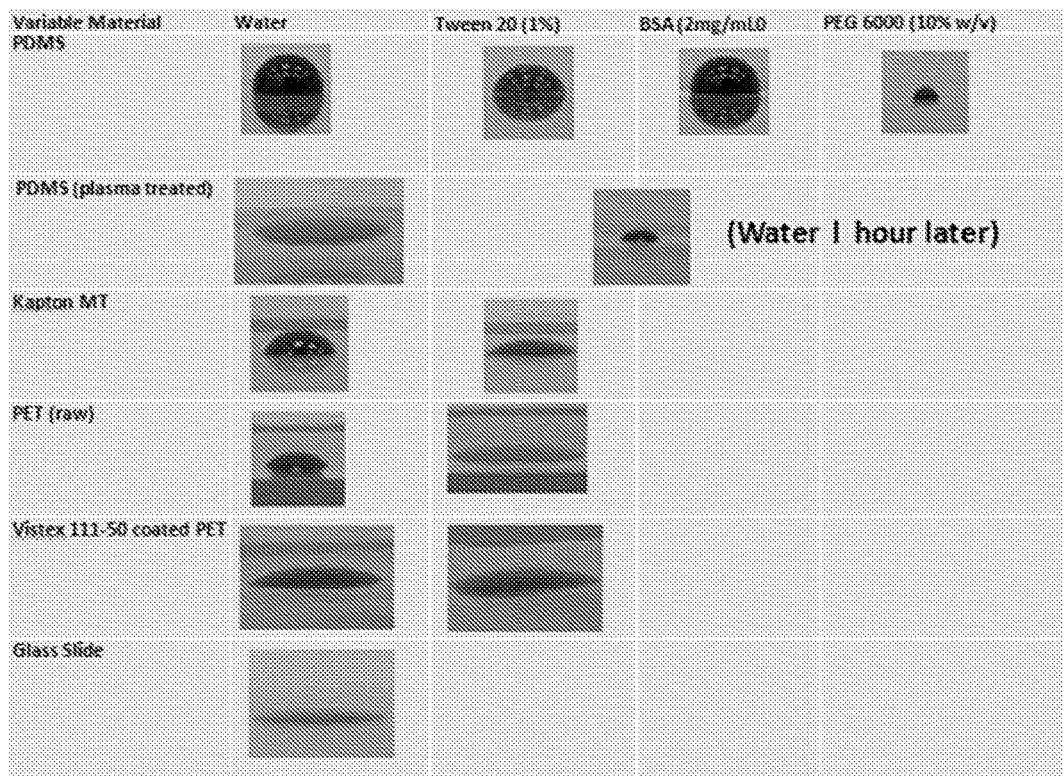
FIG. 13 shows fluid contact angles of a 10 μL droplet on various material surfaces.

FIG. 13 shows fluid contact angles of a 10 µL water droplet on various material surfaces. Examples of cartridge materials with different hydrophilic properties include plastic materials such as untreated PDMS, treated PDMS, Kapton® MT, raw polyethylene terephthalate (PET), coated PET, glass, etc. Some materials (e.g., plastic materials) are further modified with coatings (e.g., Vistex 111-50) and/or by chemical or physicochemical treatment (e.g., plasma treatment) to make them more hydrophilic. In some implementations, a given amount (e.g., a small amount that does not undesirably alter optical or kinetic properties of the sample fluid) of a detergent or other chemical material can be added to the sample fluid (e.g., used in an assay buffer). In some cases, the chemical material (e.g., Tween-20, Bovine Serum Albumin, polyethylene glycol) can alter sample fluid properties to enable easier filling of the cartridge (e.g., with less trapped bubbles, less spill, etc.). In some examples, cartridge materials can be chosen to provide one or more fluid surfaces with a given contact angle. In one example, PET can be used instead of PDMS due to its more hydrophilic properties. In another example, one or more materials with a contact angle of less than about 5°, less than about 10°, less than about 15°, less than about 20°, less than about 30°, less than about 40°, or the like can be used. In some examples, some surfaces or materials of the cartridge (e.g., materials or surfaces wetted by the sample fluid) can comprise a material with a smaller contact angle (i.e., more hydrophilic) than other materials on the cartridge.

Further, the laminated cartridge can comprise portions configured for efficient stretching upon mechanical actuation. For example, at least one of the membranes 31, 32 (e.g., top membrane 31) can be configured to stretch efficiently to allow the fluid to be moved from one chamber to another using mechanical actuation. In some cases, the membrane can stretch or "blister".

The cartridge and chambers can be held against the heaters or the heater blocks by the pressures imposed by the actuators. For example, in a configuration where heating is provided by heater blocks adjacent the thermally conductive bottom 32, the cartridge can be held down against the heater blocks (e.g., heater blocks 12 and 13). Significant counter-pressure can be exerted by the actuator adjacent to the chamber filled with PCR fluid (i.e., the actuator located on the same side or portion of the cartridge as the chamber that is filled with PCR fluid).

The cartridge can be provided as a rigid structure. Alignment features 38 can be used to mechanically hold the individual laminate layers in place with respect to each other. The alignment features can include, but are not limited to, screws, nuts and bolts, heat stakes, pegs, adhesive filling, etc. In some implementations, an outer casing can be provided to allow easier handling and alignment (e.g., when inserting the cartridge into a durable instrument or analyzer).

The outer casing can also provide features for filling the device and for valving the fluid to prevent leaking during PCR (e.g., using fill/vent ports and pinch points, as described elsewhere herein). The outer casing can be coupled to the laminate structure using, for example, the alignment features 38. In some cases, the outer casing can be coupled to the laminate structure without using the alignment features 38. For example, the outer casing can have flanges for gripping the laminate structure. The outer casing and the laminate structure can also be provided with mating features (clips, clasps, connectors, heat stakes, snap locks, etc.) for forming a secure mechanical connection. In some cases, the outer casing can comprise one or more secondary rigid structures or covers. For example, a first rigid cover 35 can be provided. In some examples, a second rigid cover 36 (e.g., as shown in FIG. 3) can be provided. In some configurations, the rigid cover can be configured to provide adequate heat transfer. In some cases, cartridges can comprise one or more alignment fixtures (e.g., alignment fixture 48 in FIG. 4). The alignment fixture may or may not be a part of the outer casing. The alignment fixture can be used for assembly and/or manufacturing. In some implementations, the alignment fixture can serve as a protective cover without providing rigid structure. In some implementations, the alignment fixture can be used for assembly/manufacturing and does not serve as a protective cover. For example, rigid covers and/or protective covers are not useful on surfaces where the cartridge directly contacts heater block(s). In further implementations, the alignment fixture can provide rigid structure. In yet other implementations, the alignment fixture can have an optical function, as described in greater detail in relation to FIG. 15.

In some examples, a cardboard sheet (or a sheet or layer of any other suitable material, including disposable and/or biodegradable polymers, paper and pulp) can be coupled (e.g., bonded to, snapped onto, clipped onto, etc.) to the laminated structure for support. In some cases, the cardboard sheet can be formed as front and/or back covers. In other cases, the cardboard sheet can be shaped differently from the laminated cartridge. For example, the cardboard sheet can be rectangular and support a laminated structure with a more complex shape (e.g., as shown in FIG. 4). Further, the cardboard sheet(s) can be tightly or loosely coupled to the laminated cartridge. The cardboard sheet(s) can cover an area that is larger, equal to or smaller than the projected area of the laminated cartridge. For example, the cardboard sheet(s) can provide support to only a portion of the laminated cartridge. In further examples, a cardboard box can be used to protect the laminated structure (e.g., as outer casing). Implementations of the laminated cartridge (e.g., with or without outer casing, cardboard backing, etc.) may be all disposable. In some implementations, the laminated structure can be separable from its support structure (e.g., backing and/or casing components). For example, the laminate structure can be all disposable while at least a portion of the support structure can be reusable. In some cases, the support structure can serve to couple the laminated cartridge to one or more other cartridges and/or to a durable instrument.

The laminated cartridge can comprise portions configured for transmitting optical signals. For example, at least one of the membranes 31, 32 (e.g., top membrane 31) can be positioned adjacent to optical excitation device(s) and detector(s) and formed of an optically transparent or clear material configured for transmitting optical signals 40 incoming to and outgoing from the sample. For example, an optically clear top membrane 31 can be used to transmit light from a light source to the sample (e.g., optical excitation) and to transmit light from the sample to a detector or readout (e.g., fluorescence emission).

In some implementations, the sample fluid can be optically detected in one or more of the PCR chambers (e.g., chambers 4 and 5). For example, fluorescence excitation and readout of the fluid can be accomplished by providing an optically transparent layered sheet or membrane formed of a material that allows excitation and readout to be made directly in a PCR well (also "chamber" herein) through the sheet or membrane. For example, a plastic or polymeric material such as polyester or PET can be used as the optically transparent material. In some cases, one or more laminate layers (e.g., the layered sheet or membrane, covers, etc.) can be partially formed from an optically transparent material (e.g., see FIG. 4). For example, the optically transparent material can be provided in regions of the laminate layers that are located directly in an optical path to/from the well.

Figure 7:
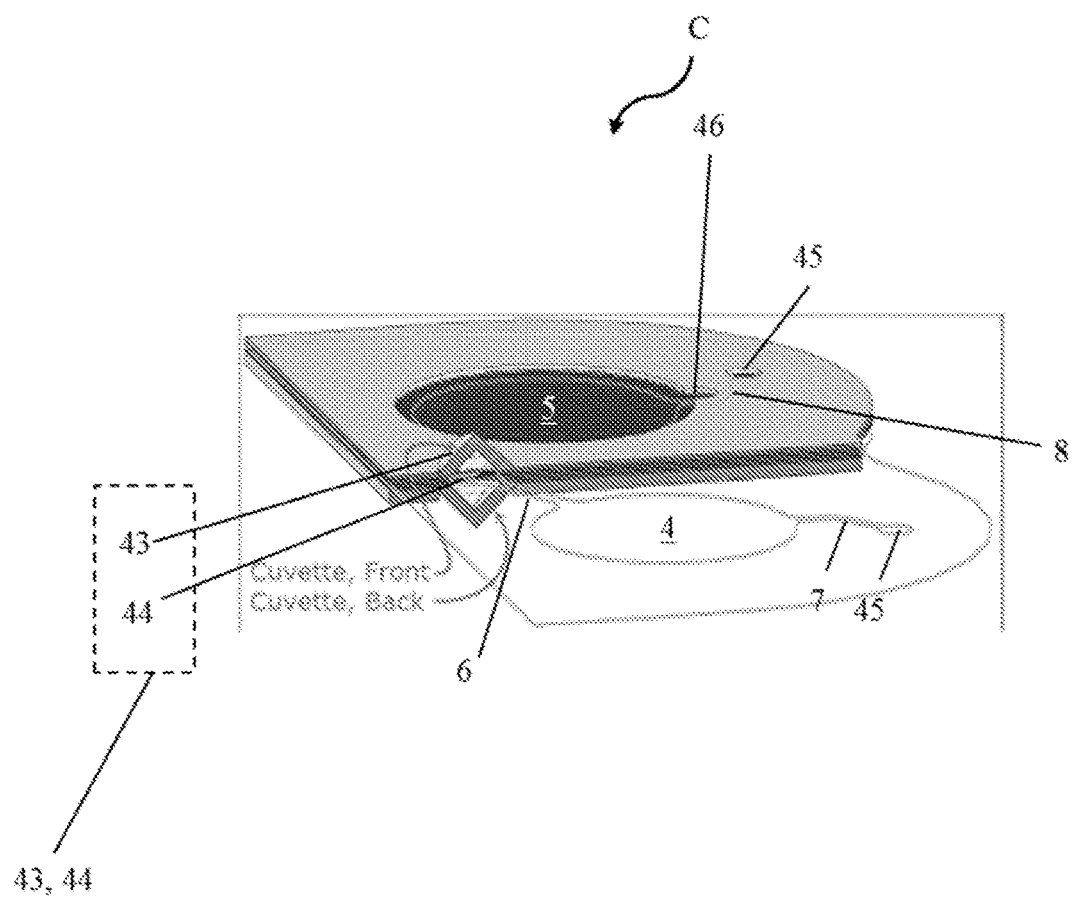
FIG. 7 are cut-away and contour views of an assembled laminated cartridge with an optical window embedded.

In other implementations, the sample fluid can be optically detected outside of the chamber(s), such as, for example, within any of the fluid flow paths (e.g., see FIGS. 4, 5 and 7). In one embodiment, a separate chamber forms within the fluid flow path (e.g., in the fluid channel 6 between the fluid chambers 4 and 5) and a corresponding optical window can be created in the laminate structure to interrogate the fluid in the separate chamber (collectively referred to as a "cuvette" herein). In this configuration, an optically transparent layered sheet or membrane is not needed, as the optical window can provide a direct optical path to the separate chamber. An advantage of the optical window can be, for example, that both the top membrane 31 and the bottom membrane 32 can be formed of thermally conductive materials, thus enabling two-sided heating without loss of optical detection capability. In some cases, sample interrogation in the separate chamber enables optical detection with higher resolution (e.g., due to size of volume interrogated, turbulence intensity, etc.). The optical window can be adapted to fit various form factors (e.g., flat form factor).

In yet other implementations, combinations of the above configurations can be used. For example, an optically transparent layer is useful to interrogate the fluid in the separate chamber without the need for a separate optical window (e.g., enabling a substantially flat form factor).

With continued reference to FIG. 3, the cartridge can be configured without a separate optical window or cuvette. In this configuration, optical readout can be made directly in one (or both) of the wells (e.g., wells 4 and 5). For example, optical excitation/readout can be provided to/from one (or both) of the chambers 4 and 5 through the actuation buttons 37 and 39, respectively. In some examples, the actuation buttons 37 and/or 39 can be at least partially formed of an optically transparent material. In other examples, the actuation buttons 37 and/or 39 can comprise one or more conduits for transmitting optical signals to and from the well(s).

FIG. 4 is an exploded view of separate layers of the layered cartridge C that includes an embedded optical window 43 with portions 43a, 43b, 43c, 43d, 43e, 43f, 43g and 43h. The optical window provides an optical path to a chamber 44 located in a fluid path (e.g., a fluid flow defined within the combined PSA layers 33, 34 between the membranes 31 and 33). In one configuration, the chamber 44 is located in the fluid path 6 between the fluid chambers 4 and 5. Together, the optical window 43 and the chamber 44 can form a cuvette 43, 44.

In this example, a secondary rigid outer structure 35 and an alignment fixture 48 (e.g., for assembly/manufacturing) can be bonded with PSA. The secondary rigid outer structure 35 can serve as a front cover. In this example, a rigid bottom cover is not provided as the bottom of the laminate cartridge is placed directly onto heater block(s). The alignment fixture 48 may or may not serve as a (protective) bottom cover. In some examples, the positions of the rigid cover 35 and the alignment fixture 48 can be reversed (e.g., depending on which cartridge surface(s) are heated). In some examples, the rigid cover 35 can be substituted by an alignment fixture or removed altogether (e.g., to enable two-sided heating). In some examples, the alignment fixture 48 is not provided. PSA layer 41 can be used between the front cover 35 and the front membrane 31. A PSA layer 42 can be used between the alignment fixture 48 and the back membrane 32. In other examples, the PSA layers can be bonded using other techniques known in the art, as described elsewhere herein.

With continued reference to FIG. 4, the cartridge laminate layers can further comprise one or more fill or vent ports 45 with portions 45a, 45b, 45c, and 45d provided, for example, on the laminate layers 35, 41, 31 and 33, 34, respectively. Fill/vent ports can be provided for a subset of cartridge chambers, or for all cartridge chambers (e.g., both of the chambers 4 and 5). Each fill/vent port 45 can be used to fill a corresponding chamber with fluid, to withdraw fluid from a corresponding chamber, to vent pressurized gas and/or fluid from a corresponding chamber, or any combination thereof. The fill/vent ports can be in fluid communication with one or more other chambers (e.g., a pre-PCR preparation chamber, filter chamber, waste chamber, etc.), a syringe needle, external or internal tubing, or any combination thereof. In some examples, more than one fill/vent port can be provided per chamber to enable multiple fluid connections with different cartridge or external components. In some implementations, access to the fill/vent port (and thus the corresponding chamber) can be enabled from top and/or bottom surfaces of the cartridge. For example, the fill/vent port can span one or more laminate layers (e.g., from the top cover 35 to the combined PSA layers 33, 34). In other implementations, the fill/vent port can be provided within a subset of the laminate layers. For example, filling and/or venting access can be enabled from a side surface of the cartridge.

The cartridge laminate layers can comprise one or more pinch points 46 with portions 46a, 46b and 46c provided, for example, on the laminate layers 35, 41 and 33,34, respectively. Pinch points can be provided for a subset of cartridge chambers, or for all cartridge chambers (e.g., both of the chambers 4 and 5). Each pinch point 46 can be used to seal a corresponding chamber (e.g., after completion of fluid filling, fluid withdrawal, gas or fluid venting, etc.). The sealing can be permanent or reversible. In an example, one of the chambers can be sealed after filling, while another one of the chambers can be periodically vented. Prior to pinching or compression (e.g., by an actuator on a durable instrument), the pinch points on the chambers 4 and/or 5 can provide fluid communication between the chambers and the fill/vent ports 45 via the channels 7 and/or 8, respectively. The pinch points can also provide fluid communication with one or more other chambers (e.g., a pre-PCR preparation chamber, filter chamber, waste chamber, etc.) or external or internal tubing instead of, or in addition to the fill/vent ports 45. In some examples, more than one pinch point can be provided per chamber to enable closing of fluid connections with different cartridge or external components. In some implementations, pinching or compression of the pinch point can be enabled from top and/or bottom surfaces of the cartridge. For example, the pinch point can be compressed through one or more laminate layers (e.g., from the top cover 35 to the combined PSA layers 33, 34, from the alignment fixture 48 to the combined PSA layers 33, 34, or both). The pinch point can be pinched or compressed by locating the cartridge adjacent to one or more actuators. In some examples, the actuator(s) can pinch or compress the pinch point(s) from a top surface of the cartridge, from a bottom surface of the cartridge, or both.

In configurations comprising the cuvette, the size and/or shape of the optically interrogated volume enables adequate optical detection. In one embodiment, the optically interrogated volume is configured to decrease or minimize its contribution to dead volume of PCR (e.g., fluid volume that is not brought to temperature during any one PCR cycle). In some examples, the interrogated volume outside of one or more PCR chambers (e.g., outside of a heated PCR chamber) can be less than about 5% or less than about 10% of the total PCR fluid volume in the cartridge.

FIG. 5 shows front, back and side views of the assembled laminated cartridge C with the optical window 43 embedded. Together with the chamber 44, the optical window can form the cuvette 43, 44. The cartridge further comprises the chambers 4 and 5 with respective fill/vent ports 45 and respective pinch points 46.

Figure 15:
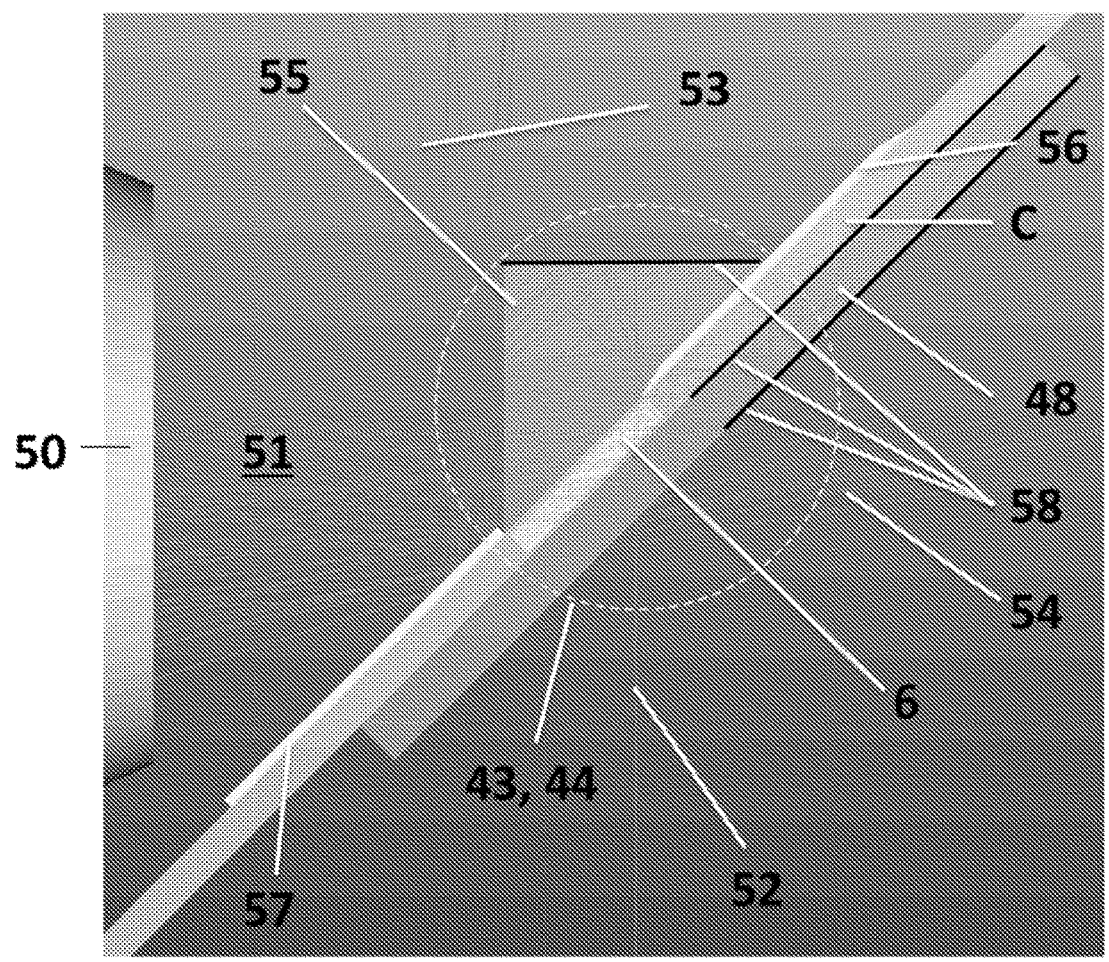
FIG. 15 shows a cartridge with optical components.

FIG. 15 shows the cartridge C (e.g., a polyester cassette) with optical components. The optical window 43 can be used for interrogating a sample volume (e.g., to direct light into an interrogation volume or sample channel, such as the chamber 44 in the sample channel 6). In some cases, the optical window 43 and the interrogated volume can form the cuvette (e.g., cuvette 43, 44). In this example, a beam-emitting apparatus or light source 50 (e.g., an excitation source) illuminates the cartridge C with an excitation beam 51. At least a portion of the excitation beam is transmitted through the optical window 43 to the chamber 44 and results in an emission signal generated in the chamber 44. In this example, the emission beam 52 is directed toward a detector (not shown) located, for example, at about 90° angle from the excitation beam. In other examples, alternative beam geometries can be used (e.g., with detection paths directed in various directions other than the source path 51, 53 and 54). A portion of the excitation beam 51 can be scattered, absorbed or otherwise lost, as shown by the source path in FIG. 15. Upon reaching the optical window 43, the excitation beam can be transmitted and absorbed by the sample fluid in the chamber 44, absorbed as heat in the cartridge, and/or transmitted through the cartridge with being absorbed. The light that is not absorbed within the cartridge can exit as a beam 54. A portion of the excitation beam 51 can be scattered or reflected away from the cartridge as beams 53 instead of being transmitted into or through the cartridge. Any description herein in relation to a (light) beam applies to light beams that are collimated, as well as light beam that are not collimated, at least in some implementations. Further, any description herein in relation to a (light) beam applies to individual light rays, and vice versa, at least in some implementations. Still further, any description of optical elements herein in relation to optical detection using the optical window 43, the chamber 44 and/or the cuvette 43, 44 applies to optical detection in one or more PCR chambers or elsewhere on the cartridge without the use of the optical window 43 at least in some implementations. In some implementations, the optical components can be packaged to allow the cartridge to be inserted and removed from a durable instrument without obstacles. In some cases, one or more features (e.g., the optical components) can fit into a mating receiving feature on the durable instrument to allow for improved positioning.

The source path can be affected and/or guided by optical components in the optical window 43 and/or the cartridge C in order to improve utilization of the excitation light and enhance transmission of light into the chamber 44. Further, the source path can be affected and/or guided by optical components in the optical window 43 and/or the cartridge C in order to direct the excitation light 51, 53 and 54 away from the detection direction 52. In some implementations, the optical window 43 can comprise light guiding elements such as, for example, prisms, lenses, or Fresnel lenses. For example, the optical window can comprise a prism 55 (e.g., a prism formed from a cyclo-olefin copolymer or other optically suitable material can be bonded to a top film of the optical window 43 or to a top film of the cartridge C). In some implementations, optical surfaces (e.g., surfaces facing the source path or a portion of the source path) can include anti-reflective coatings to help transmit the excitation light to the interrogation volume or sample channel (e.g., chamber 44, or one or more PCR chambers). In some implementations, foils 56 and 57 (e.g., light-blocking foils) can be used on one or more surfaces (e.g., surfaces of the cartridge directed toward the excitation light 51). Further, in some implementations, optical surfaces that allow scattered excitation light into the detection path (e.g., detection path 52) can be coated or blocked using foil, paint or other structures. For example, black-painted surfaces 58 can be provided on one or more interfaces of the optical plate or alignment fixture 48 (e.g., a cyclo-olefin copolymer or other optically suitable material can be bonded to a bottom (back) surface or film of the cartridge C) and/or on one or more interfaces of the prism 55. Light-directing features (e.g., lens or prism) and features to block stray light from the excitation source (e.g., foil or coatings) can be used separately or in combination (e.g., synergistically combined).

FIG. 6 is an exploded view the 'blister pack" disposable cartridge C with three layers comprising the layered sheets or membranes 31 and 32 and the combined PSA layers 33, 34. The cartridge further comprises the channels 7 and 8 for filling and extracting sample fluid sample from the chambers 4 and 5, respectively, and the channel 6 connecting the chambers 4 and 5. In some implementations, a pinch point (not shown) is provided on the connecting channel 6. Such a pinch point can be reversible to allow for thermocycling of the sample fluid between the chambers 4 and 5.

FIG. 7 are cut-away and contour views of the assembled laminated cartridge C with the optical window 43 embedded. Together with the chamber 44, the optical window can form the cuvette 43, 44. The cuvette may or may not protrude from the cartridge surface as shown in FIG. 7. The cuvette, or any other optical detection configuration described herein, can enable real-time PCR to be recorded. The cartridge further comprises the connecting channel 6 connecting the chambers 4 and 5, the fill/vent ports 45, the pinch point 46, and the channels 7 and 8 for filling and extracting sample fluid sample from the chambers 4 and 5, respectively.

Figure 8:
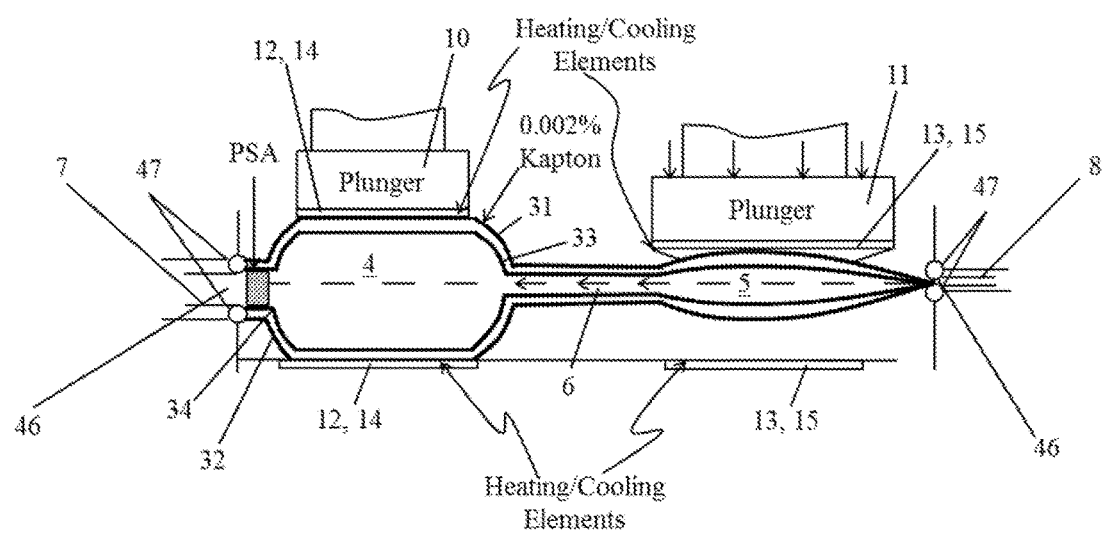
FIG. 8 shows a cartridge thermally modeled in Comsol assuming one-sided or two-sided heating through 50 micron (50 μm) thick polyimide film(s).

FIG. 8 shows a cartridge thermally modeled in Comsol assuming one-sided or two-sided heating through polyimide membrane(s). The polyimide membrane(s) can comprise one or more types of Kapton®, such as, for example, Kapton® MT. The polyimide membrane(s) can be about 50 micron (50 μm) thick. The cartridge comprises the channels 6, 7 and 8, actuators, pinchers or pistons 47 for pinching/compressing the pinch points 46, plungers 10 and 11 for compressing the top walls of the chambers 4 and 5, respectively, a pair of heating/cooling elements 12, 14 for heating top and bottom walls of the chamber 4, and a pair of heating/cooling elements 13, 15 for heating top and bottom walls of the chamber 5. In this example, aluminum backed heating/cooling elements 12, 14 and 13, 15 can be used. The chambers 4 and 5 can be formed from laminate layers. The top wall of each chamber can comprise the membrane 31 (e.g., a Kapton® MT membrane) and the PSA layer 33. The bottom wall of each chamber can comprise the PSA layer 34 and the membrane 32 (e.g., a Kapton® MT membrane). A heat conductive material, such as a 50 μm (0.002 inch) thick Kapton® MT interface, can be used between the chambers, and the heating/cooling elements 12, 14 and/or 13, 15. When one-sided heating is used, only one of the membranes 31 and 32 can be formed of a heat conductive material. For example, the top membrane 31 can be formed of PDMS while the bottom membrane 32 can be formed of Kapton® MT. When two-sided heating is used, both membranes 31 and 32 can be formed of a heat conductive material. For example, both membranes 31 and 32 can be formed of Kapton® MT.

In an example, a nominal sample volume of 60 μL is contained within cartridge chambers with a total (combined) internal volume of about 60 μL. Each of the chambers 4 and 5 can have an undeformed internal volume of about 30 μL with a height (also "reduced sample volume height" herein) of about 250 μm. Upon actuation, one of the chambers (i.e., the chamber on the actuated side) is compressed and deformed (e.g., to a fraction of its undeformed internal volume). The sample volume is transferred to the other chamber, which is expanded and deformed. The deformed internal volume of this chamber can be about 60 μL (e.g., same as the sample volume). Upon subsequent actuation, the chamber that was previously expanded is compressed, the chamber that was previously compressed is expanded, and the situation is reversed. In some examples, the lower the height of the chamber, the larger the area that the sample volume can be spread out over, leading to enhanced heat transfer rates. For example, large values of surface area to height or surface area to volume ratios of the chambers can lead to increased heat transfer rates, and consequently decreased ramp times. In some examples, the height of one or more of the chambers is less than about 500 μm, less than about 400 μm, less than about 300 μm, less than about 250 μm, less than about 200 μm, and the like.

Figure 9A:
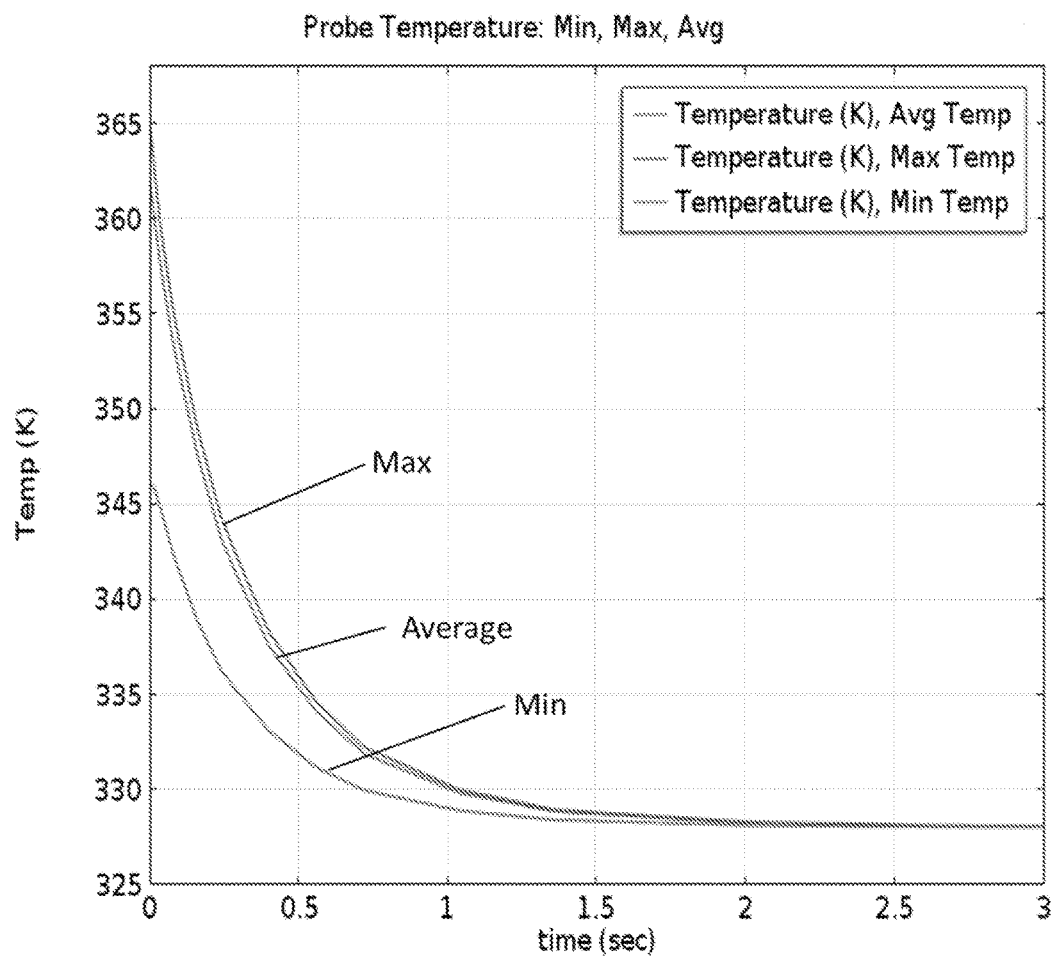
FIG. 9A provides thermal modeling results for the cartridge in FIG. 8 with two-sided heating, showing that temperatures are reached within 2 seconds.
Figure 9B:
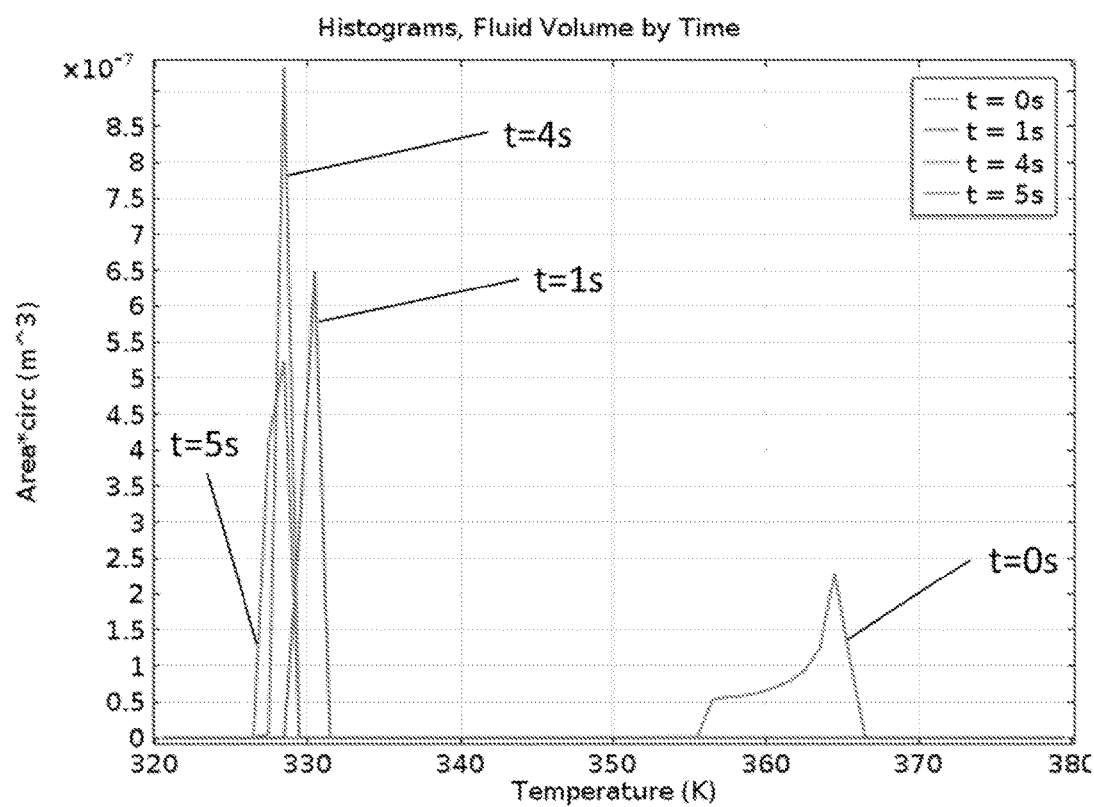
FIG. 9B shows a histogram of fluid temperatures entering the cold chamber (55° C.) from the hot chamber (95° C.), as modeled in FIG. 9A.
Figure 10A:
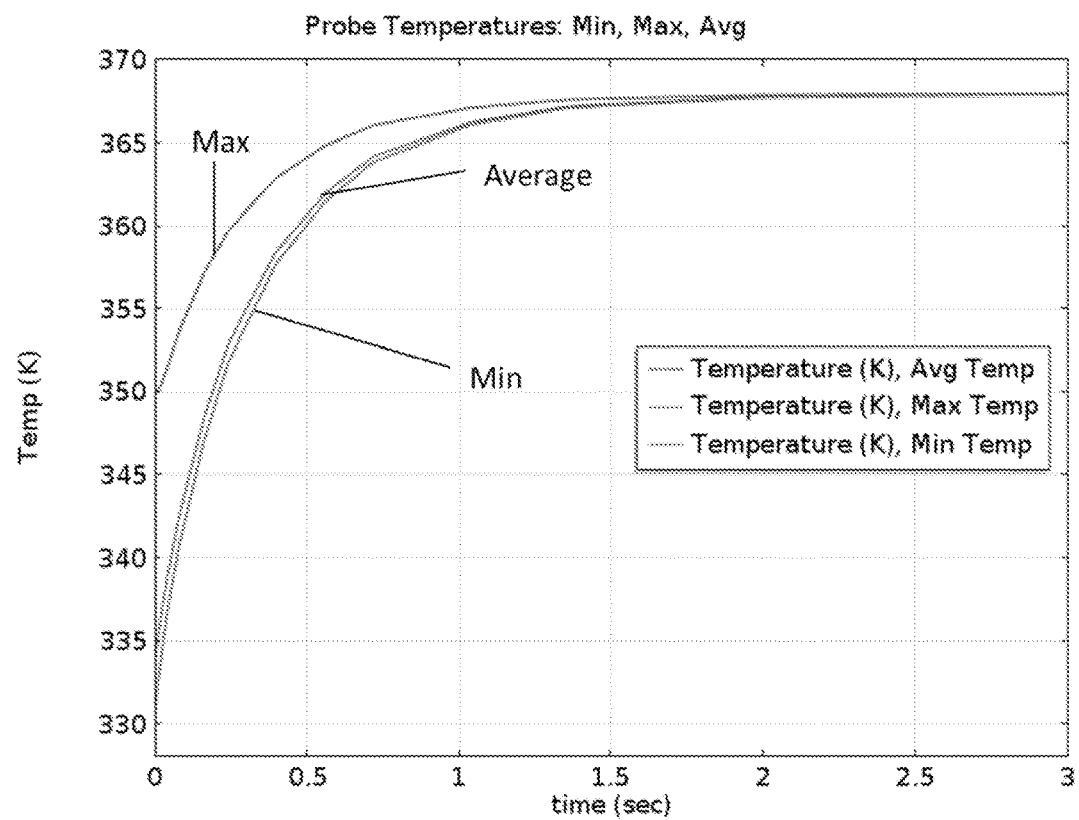
FIG. 10A provides thermal modeling results for the cartridge in FIG. 8 with two-sided heating, showing that temperatures are reached within 2 seconds.
Figure 10B:
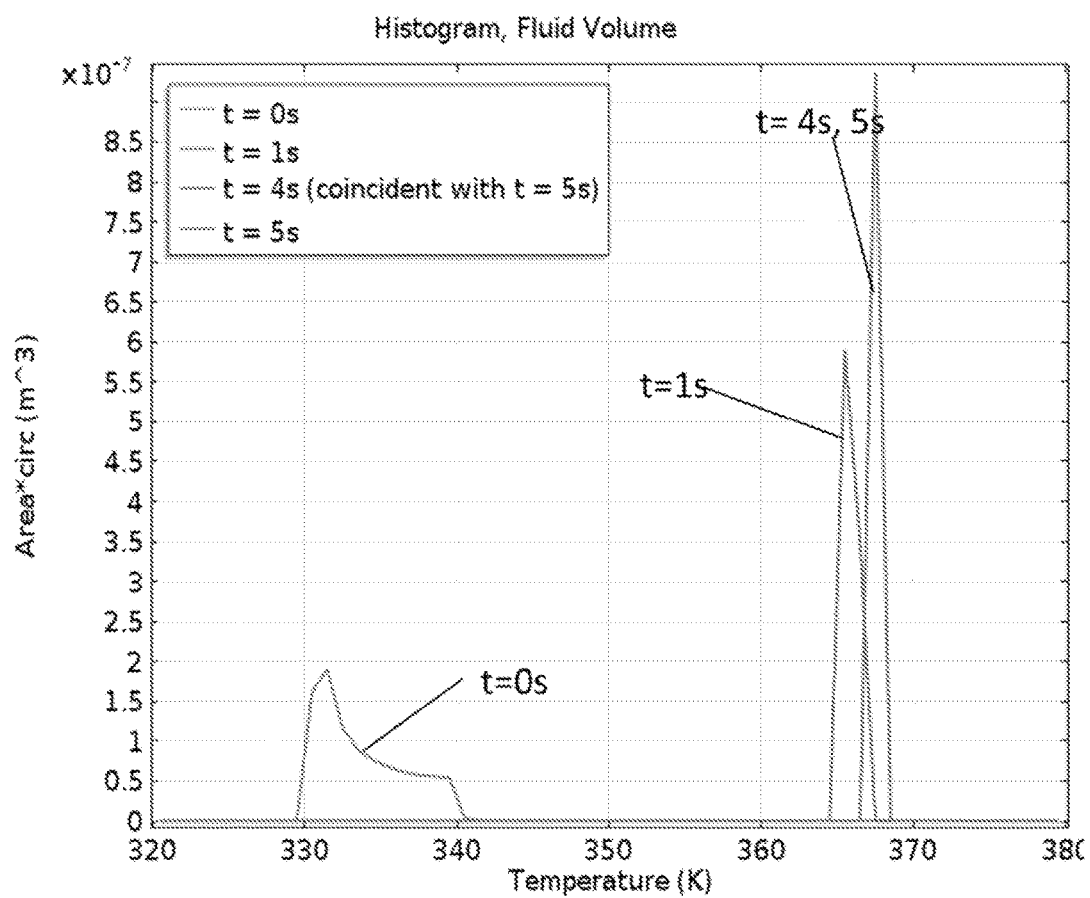
FIG. 10B shows a histogram of fluid temperatures entering the hot chamber (95° C.) from the cold chamber (55° C.), as modeled in FIG. 10A.
Figure 11A:
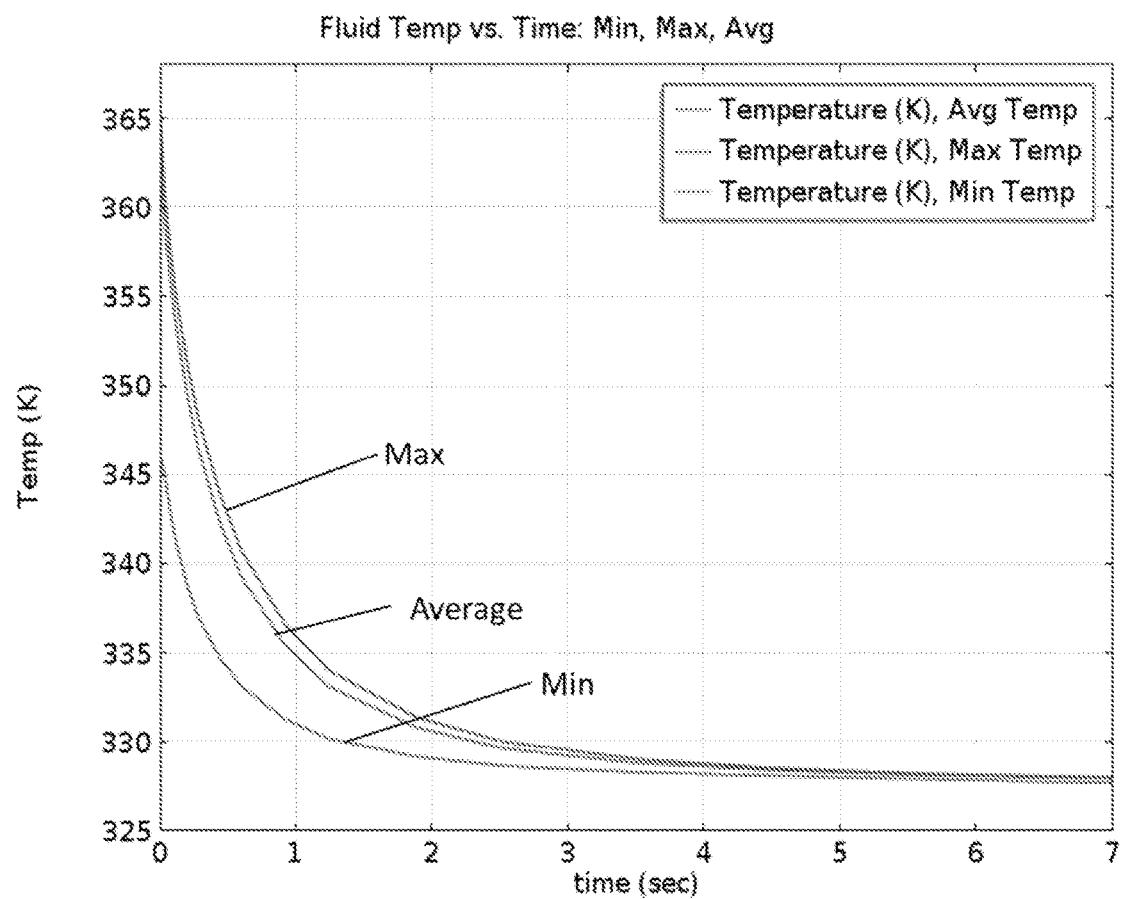
FIG. 11A provides thermal modeling results for the cartridge in FIG. 8 with one-sided heating, showing that temperatures are reached within 4 seconds.
Figure 11B:
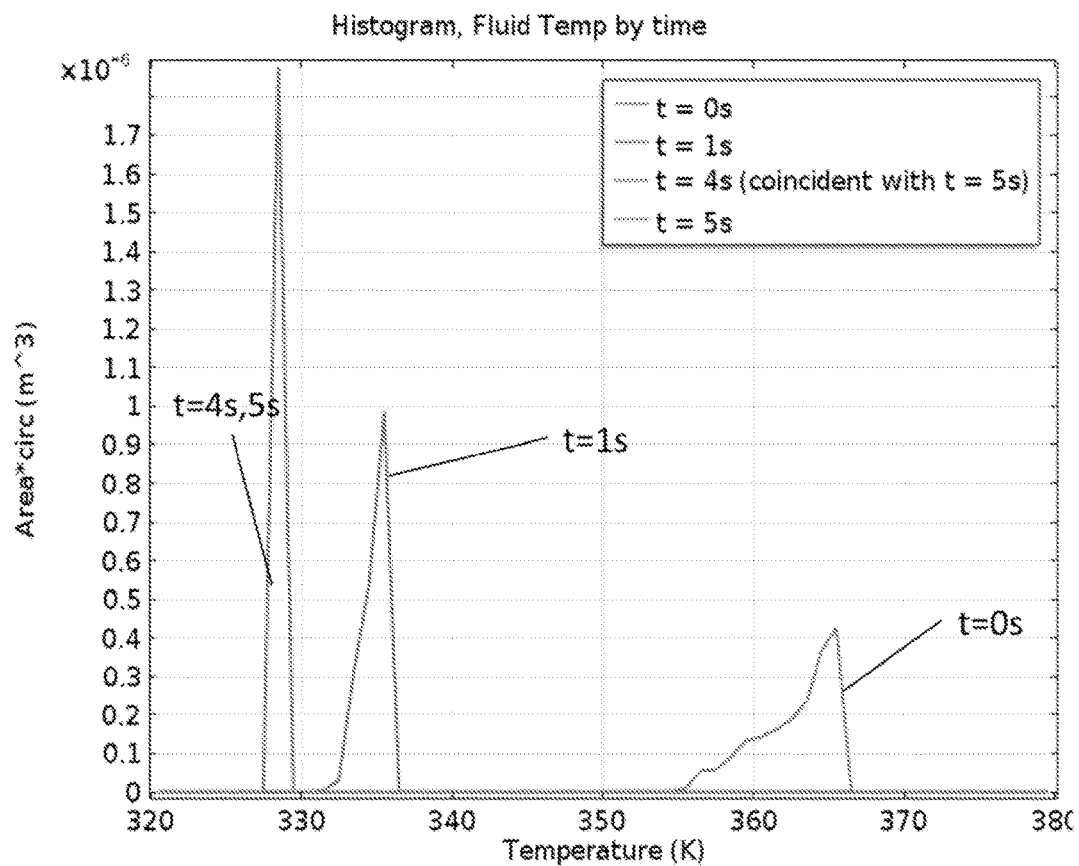
FIG. 11B shows a histogram of fluid temperatures entering the cold chamber (55° C.) from the hot chamber (95° C.), as modeled in FIG. 11A.
Figure 12A:
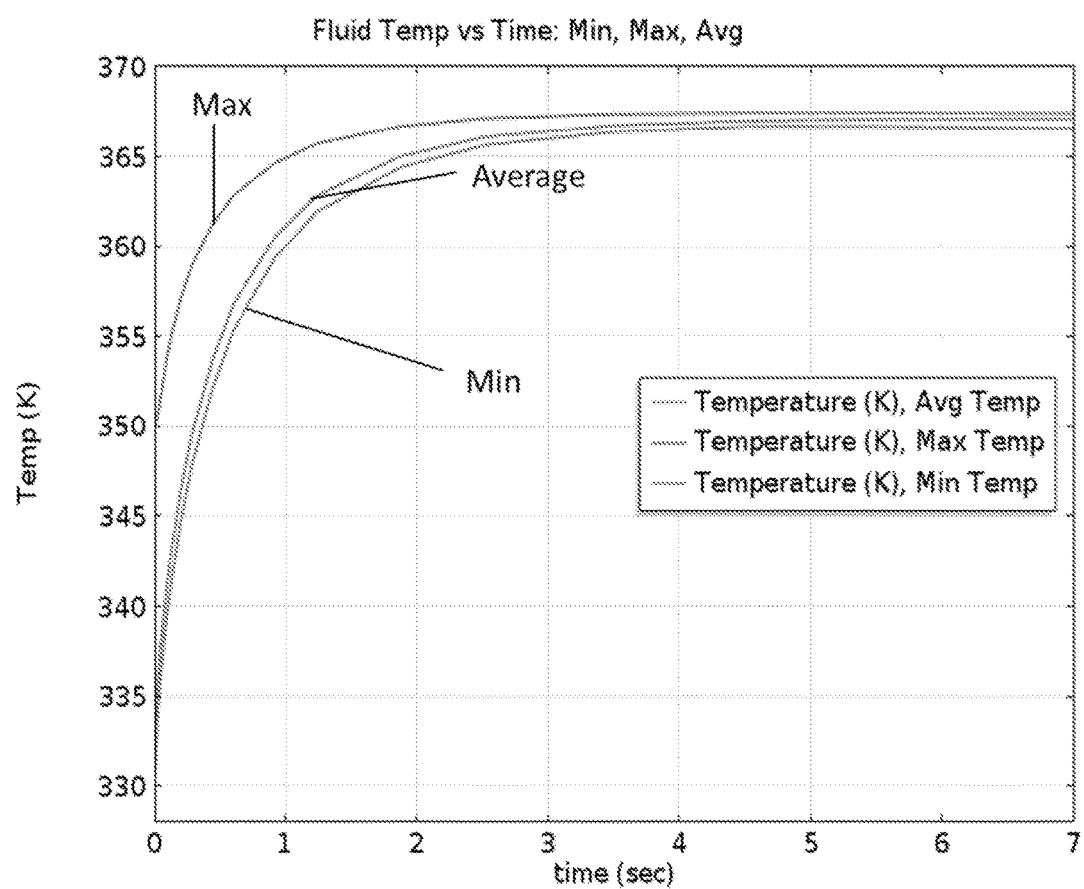
FIG. 12A provides thermal modeling results for the cartridge in FIG. 8 with one-sided heating, showing that temperatures are reached within 4 seconds.
Figure 12B:
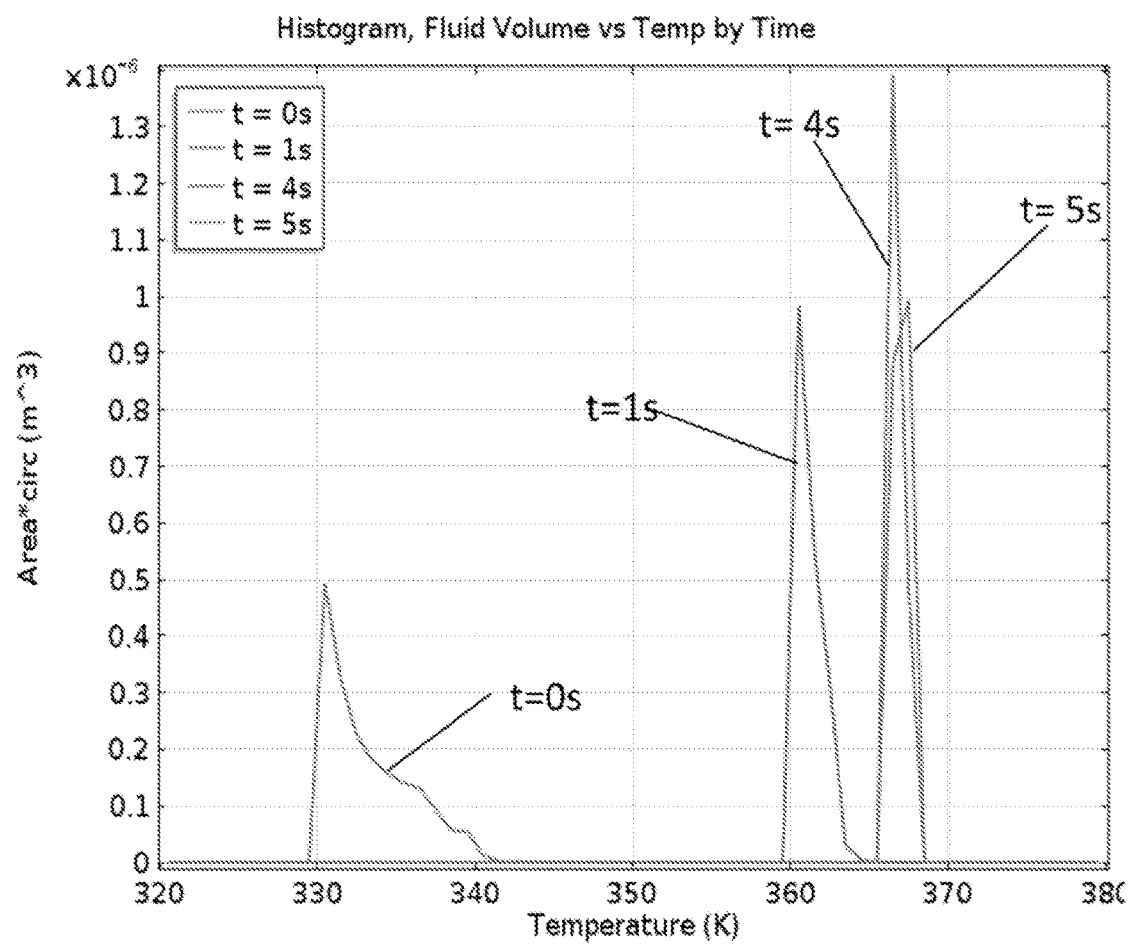
FIG. 12B shows a histogram of fluid temperatures entering the hot chamber (95° C.) from the cold chamber (55° C.), as modeled in FIG. 12A.

FIGS. 9, 10, 11 and 12 provide thermal modeling results for the cartridge in FIG. 8. In FIGS. 9 and 11, fluid temperature in the cold chamber 4 immediately after fluid transfer from the hot chamber 5 at 95° C. is shown on the left, and a histogram of temperatures of the fluid entering the cold chamber 4 is shown on the right. In FIGS. 10 and 12, fluid temperature in the hot chamber 5 immediately after fluid transfer from the cold chamber 4 at 55° C. is shown on the left, and a histogram of temperatures of the fluid entering the hot chamber 5 is shown on the right. The ambient temperature can be about 23° C. Two-sided heating in FIGS. 9 and 10 can result in reaching desired cartridge chamber temperatures within about 2 seconds. One-sided heating in FIGS. 11 and 12 can result in reaching desired cartridge chamber temperatures within about 4 seconds.

Figure 14:
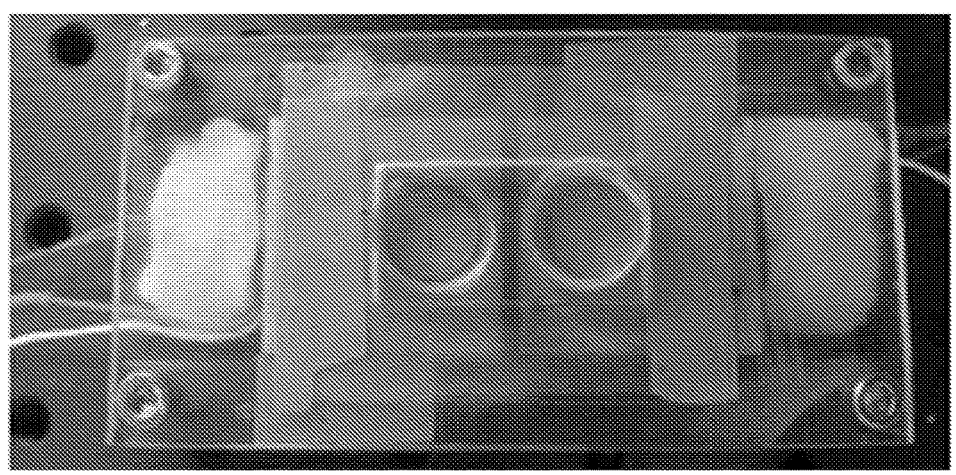
FIG. 14A provides a working embodiment of a laminated cartridge.
FIG. 14B illustrates a recorded demonstration of PCR in a laminated structure.
Figure 14:
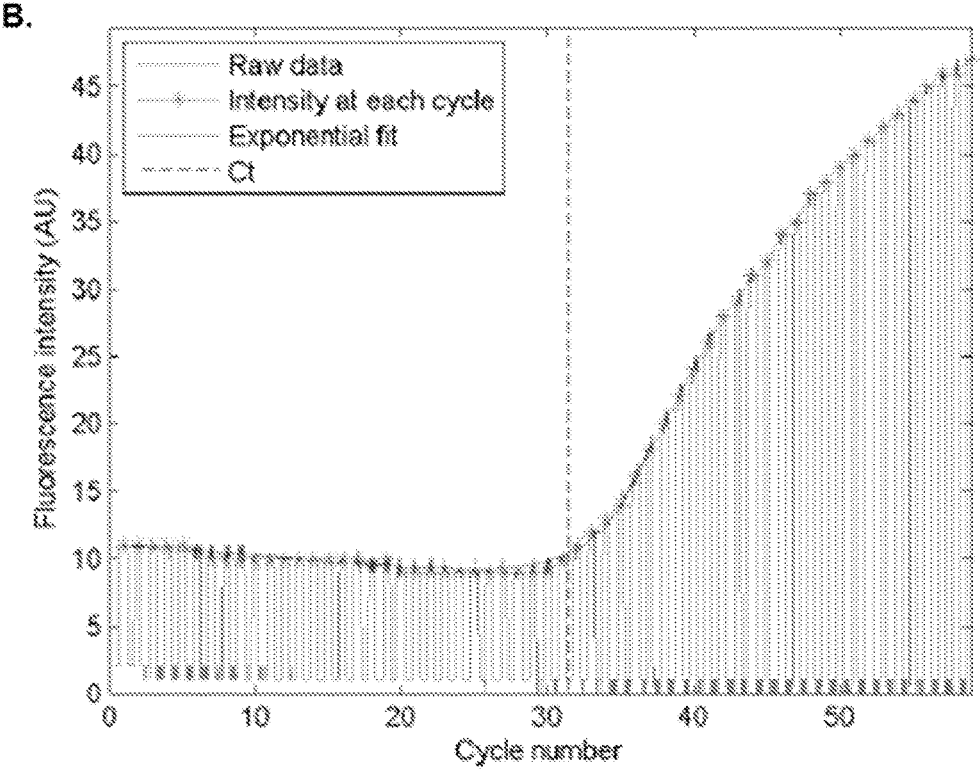

FIG. 14 illustrates a recorded demonstration of PCR in a four-layer laminated structure without a separate optical window, such as, for example, the laminate structure in FIG. 3. The fluorescence can be read out through the low-temperature actuation button 37 through the PET top layer 31. The cartridge can further comprise the laminate layer 31

(e.g., comprising a 50.8 μm thick PET film), the laminate layer 33 (e.g., comprising a 127 μm thick 3M 96042 Double-Coated Silicone Adhesive layer), the laminate layer 34 (e.g., comprising a 127 μm thick 3M 96042 Double-Coated Silicone Adhesive layer), and the laminate layer 32 (e.g., comprising a 50.8 μm thick Kapton® MT film). In this example, the undeformed thickness (also "reduced sample volume height" herein) is about 254 μm, and the 50 μL sample volume comprises about 21.25 μL of $10^5$ DNA/mL B. Atro (i.e., total concentration of $4.25 \times 10^4$ DNA/mL), 25 μL TaqMan® Master Mix, 1.25 μL of $10^5$ micromolar (μM) FAM probe, 1.25 μL of 36 μM B. Atro forward primer, and 1.25 μL of 36 μM B. Atro reverse primer. An inflection point 49 measured fluorescence intensity as a function of cycle number indicates successful PCR amplification of the sample. In this example, PCR temperatures are approximately 60° C. (333 K) and approximately 95° C. (368 K).

Laminate layers (e.g., layered sheets or membranes, PSAs, etc.) of the disclosure can have a given thickness. Laminate layers can have different thicknesses. In some cases, one or more laminate layers can have the same thickness. For example, PSA layers can have a first thickness and membranes can have a second thickness. In some cases, laminate layers can have the same thicknesses. In some implementations, a subset of the laminate layers can a thickness based on required mechanical integrity. For example, laminate layers that are exposed to heating may need to exhibit a higher mechanical integrity (e.g., coupled to heat resistance) than laminate layers that are not exposed to heating. In another example, laminate layers that are exposed to a higher degree of stretching and/or compression may need to exhibit a higher mechanical integrity than laminate layers that experience less stress (e.g., membranes may need to withstand a higher mechanical stress than PSAs). Further, the thickness of each laminate layer can vary across the area of the laminate layer. For example, the laminate layer can be thicker in an area that is exposed to a higher degree of stress (e.g., chamber pressure, tension, compression strength). In another example, the laminate layer thickness can be reduced in areas where optical detection, heat transfer, pinching, filling, extraction, venting and/or other cartridge manipulations are performed. As described elsewhere herein, laminate layer thickness can further be used to define chamber volume. For example, the thickness of one or more PSA layers can be larger than the thickness of one or more membranes in situations where thicker PSA layers are used to implement chambers with larger internal volume(s). In another example, membrane thickness is adjusted to achieve a given mechanical integrity and/or heat transfer performance, while PSA thickness is adjusted to achieve a given internal volume of chambers, or vice versa. Further, membrane thickness and/or PSA thickness can be adjusted to achieve a given mechanical integrity, a given heat transfer performance, a given internal volume of chambers, or any combination thereof.

In some examples, a laminate layer, or a portion thereof, can have a thickness of at least about 10 μm, at least about 20 μm, at least about 30 μm, at least about 40 μm, at least about 50 μm, at least about 60 μm, at least about 70 μm, at least about 80 μm, at least about 90 μm, at least about 100 μm, at least about 110 μm, at least about 120 μm, at least about 130 μm, at least about 140 μm, at least about 150 μm, at least about 160 μm, at least about 170 μm, at least about 180 μm, at least about 190 μm, at least about 200 μm, and the like. In some examples, a laminate layer of the disclosure can have a thickness of less than about 10 μm, less than about 20 μm, less than about 30 μm, less than about 40 μm, less than about 50 μm, less than about 60 μm, less than about 70 μm, less than about 80 μm, less than about 90 μm, less than about 100 μm, less than about 110 μm, less than about 120 μm, less than about 130 μm, less than about 140 μm, less than about 150 μm, less than about 160 μm, less than about 170 μm, less than about 180 μm, less than about 190 μm, less than about 200 μm, and the like. In some examples, a laminate layer has a thickness of about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, or more. In an example, a membrane formed of a heat conductive material can have a thickness of about 30-70 μm or about 45-55 μm, while a PSA layer can have a thickness of about 100-150 μm or about 125-130 μm.

Multichamber Cartridges

In one aspect, provided herein are multichamber cartridges for use in a thermocycling reaction. In exemplary embodiments, a multichamber cartridge is a component of a thermocycler or cartridge-based system described herein. In one embodiment, a multichamber cartridge comprises a disposable portion of a thermocycler system. A thermocycler system, such as previously described herein accommodates one or more multichamber cartridges for performing simultaneous thermocycling reactions. In some embodiments, the multichamber cartridge comprises a first chamber for holding a fluid at a first average temperature and a second chamber for holding the fluid at a second average temperature. The second chamber is in fluid communication with the first chamber, wherein the fluid is transferred between the first chamber and the second chamber to achieve a transition from the first average temperature to substantially the second average temperature or vice versa. The first chamber and the second chamber are in fluid connection via a connecting channel. In an exemplary embodiment, a multichamber cartridge is a disposable as described previously herein, for example, a laminated disposable cartridge, and vice versa. In another embodiment, a cartridge or thermocycler as previously described further comprises or is operably connected to one or more components or elements of a multichamber cartridge as described below, for example, a buffer solution tube or blistered chamber.

An average temperature includes any temperature within 5° C. of the set temperature, for example, an average temperature for a reaction in a hot chamber set at 95° C. has a temperature from about 90° C. to about 100° C. In another embodiment, an average temperature includes any temperature within 3° C. of the set temperature, for example, an average temperature for a reaction in a hot chamber set at 95° C. has a temperature from about 92° C. to about 98° C. In another embodiment, an average temperature includes any temperature within 2° C. of the set temperature, for example, an average temperature for a reaction in a hot chamber set at 95° C. has a temperature from about 93° C. to about 97° C. In another embodiment, an average temperature includes any temperature within 1° C. of the set temperature, for example, an average temperature for a reaction in a hot chamber set at 95° C. has a temperature from about 94° C. to about 96° C. In certain instances, the temperature of a heater fluctuates between average temperature values during a thermocycling reaction. Alternatively, the temperature of a heater does not fluctuate temperature during a thermocycling reaction. A substantially average temperature includes a temperature within 5° C., 4° C., 3°

C., 2° C., 1° C. or 0.5° C. of the average temperature. The average temperature includes the temperature set in a thermocycling reaction, the temperature of a heating element (e.g., heater as described herein), the temperature of a fluid in chamber, and any combination thereof.

In one embodiment, the multichamber cartridge comprises a third chamber for holding a fluid at a third average temperature in fluid communication, directly or indirectly, with the first chamber, the second chamber, or both the first and second chambers. In another embodiment, a multichamber cartridge comprises a fourth chamber for holding a fluid at a fourth average temperature. In yet another embodiment, a multichamber cartridge comprises a fifth, sixth, seventh, eighth, ninth or tenth chamber for holding a fluid at a fifth, sixth, seventh, eighth, ninth or tenth average temperature, respectively. In various implementations, the third chamber, fourth chamber, fifth chamber, sixth chamber, seventh chamber, eighth chamber, ninth chamber, tenth chamber, or any combination thereof is an auxiliary chamber. In one example, the auxiliary chamber is a blistered chamber. In alternative implementations, the third, fourth, fifth, sixth, seventh, eighth, ninth, tenth, or any combination thereof is not held at a fixed average temperature.

In one instance, the first chamber, second chamber, third chamber, fourth chamber, fifth chamber, sixth chamber, seventh chamber, eighth chamber, ninth chamber, tenth chamber, or any combination thereof is held at an average temperature of between about 90° C. and about 110° C. for a given time during a thermocycling reaction. In one instance, the first chamber, second chamber, third chamber, fourth chamber, fifth chamber, sixth chamber, seventh chamber, eighth chamber, ninth chamber, tenth chamber, or any combination thereof is held at an average temperature suitable for denaturing nucleic acid molecules for a given time during a thermocycling reaction. In one instance, the first chamber, second chamber, third chamber, fourth chamber, fifth chamber, sixth chamber, seventh chamber, eighth chamber, ninth chamber, tenth chamber, or any combination thereof is held at an average temperature of between about 40° C. and about 75° C. for a given time during a thermocycling reaction. In one instance, the first chamber, second chamber, third chamber, fourth chamber, fifth chamber, sixth chamber, seventh chamber, eighth chamber, ninth chamber, tenth chamber, or any combination thereof is held at an average temperature suitable for nucleic acid annealing for a given time during a thermocycling reaction. In one instance, the first chamber, second chamber, third chamber, fourth chamber, fifth chamber, sixth chamber, seventh chamber, eighth chamber, ninth chamber, tenth chamber, or any combination thereof is held at an average temperature of between about 60° C. and about 80° C. for a given time during a thermocycling reaction. In one instance, the first chamber, second chamber, third chamber, fourth chamber, fifth chamber, sixth chamber, seventh chamber, eighth chamber, ninth chamber, tenth chamber, or any combination thereof is held at an average temperature suitable for nucleic acid extension for a given time during a thermocycling reaction. In one instance, the first chamber, second chamber, third chamber, fourth chamber, fifth chamber, sixth chamber, seventh chamber, eighth chamber, ninth chamber, tenth chamber, or any combination thereof is held at an average temperature suitable for nucleic acid digestion (e.g., with restriction enzymes) or ligation. In one instance, the first chamber, second chamber, third chamber, fourth chamber, fifth chamber, sixth chamber, seventh chamber, eighth chamber, ninth chamber, tenth chamber, or any combination thereof is held at an average temperature suitable for temporarily storing or cooling nucleic acid molecules, for example from about 2° C. to about 25° C.

In one embodiment, a multichamber cartridge is configured to receive a sample from a swab collection tube. In one implementation, the swab collection tube is a removable component of a multichamber cartridge. A swab collection tube retains a sample, optionally collected on a swab. For example, a sample is collected from a subject or environment and placed in a sample collection tube for storage. The sample can then be transferred to a multichamber cartridge prior to a thermocycling reaction. In one embodiment, the sample comprises nucleic acids to be amplified in an amplification reaction. In addition to a sample, the swab collection tube is configured to retain a swab solution, which includes reagents for preserving a sample, such as a biological sample, and includes, without limitation, buffer agents and salts. In another example, a swab collection tube comprises processing reagents. In one embodiment, the swab collection tube is fitted with a swab plunger for delivering a sample solution to a chamber or other component of a multichamber cartridge. In one instance, the contents of a swab collection tube, or a portion thereof, are delivered to a chamber of the multichamber cartridge via a receiving tube. In another instance, a sample is processed in the swab collection tube. For example, a sample comprising whole blood is processed to separate serum, wherein the processing reagents in the sample collection tube comprise a polymer gel and a powdered glass clot activator.

In various aspects, a sample provided to a cartridge described herein comprises one or more analytes suitable for a thermocycling reaction. Exemplary analytes include nucleic acid molecules to be amplified during a thermocycling reaction. Samples include fluid and solid samples. The sample includes any appropriate material, with any suitable origin. For example, a sample includes, without limitation, a biomolecule, organelle, virus, cell, tissue, organ, and/or organism. A sample optionally is a biological sample, such as blood, urine, saliva, sweat, seminal fluid, tissue, amniotic fluid, cerebrospinal fluid, synovial fluid, tears, fecal matter, and/or mucous, among others. A sample optionally is an environmental sample, such as a sample from air, water, or soil. In one embodiment, a sample is aqueous and optionally comprises buffering agents, inorganic salts, and/or other components known for assay solutions. Suitable samples include compounds, mixtures, surfaces, solutions, emulsions, suspensions, cell cultures, fermentation cultures, cells, tissues, secretions, and/or derivatives and/or extracts thereof. A sample includes food products. In some instances, a sample is provided to the cartridge in a processed form altered from its original state. For example, it may be necessary to lyse or permeabilize cells to release nucleic acids. Such methods include chemical (e.g., Lysozyme), mechanical (e.g., sonication), thermal, or a combination thereof. As another example, a sample comprising a pathogenic organism is chemically or thermally inactivated. In some instances, analytes (e.g., nucleic acids) of a processed sample are isolated or separated in one or more tubes or chambers of the cartridge.

In one embodiment, a multichamber cartridge comprises a receiving tube for receiving a sample. In one implementation, the sample is provided in whole or in part from a swab collection tube. In another example, a sample (optionally processed) is provided to the receiving tube directly via an opening, for example, a fill port, by any means suitable for transferring a liquid or semi-liquid solution, e.g., syringe, pipette or plunger. In one embodiment, the receiving tube is a disposable and/or removable component of a thermocycler.

In one embodiment, a multichamber cartridge comprises one or more buffer solution tubes, wherein each buffer solution tube is configured to hold one or more buffers or aqueous solutions. In one embodiment, a multichamber cartridge comprises 1, 2, 3, 4, 5, 6, 7, 8, 9, 10 or more buffer solution tubes. In an exemplary embodiment, a multichamber cartridge comprises 3 buffer solution tubes. In one instance, the multichamber cartridge is formulated to hold one or more buffers in the one or more buffer solution tubes, for example, the multichamber cartridge is manufactured with buffer solution(s) stored in the tube(s). In one embodiment, the buffers are supplied in a cartridge as aqueous solutions or as dehydrated pellets to be reconstituted with an aqueous solution. In another instance, the multichamber cartridge is supplied with buffers by a thermocycler end-user, wherein the buffer components are optimized for a specific thermocycling reaction. A buffer or aqueous solution comprise any components useful for carrying out a thermocycling reaction, e.g., a nucleic acid amplification reaction. Suitable components include, without limitation, primers, probes, polymerases, nucleotides, divalent cations, and monovalent cations. In one embodiment, a buffer solution tube holds volumes up to about 5 mL, up to about 4 mL, up to about 3 mL, up to about 2 mL, up to about 1 mL, up to about 0.5 mL, up to about 0.4 mL, up to about 0.3 mL, up to about 0.2 mL or up to about 0.1 mL. In one embodiment, one or more buffer solution tubes are disposable and/or removable components of a thermocycler.

In one embodiment, a multichamber cartridge comprises a means for delivering a buffer solution to a chamber of the cartridge. For example, a buffer solution is delivered to a chamber of the cartridge by application of a plunger. In the instances wherein a multichamber cartridge comprises a plurality of buffer solution tubes, one or more buffer solutions are delivered to one or more chambers via a rotating plunger. In one embodiment, the plunger is a disposable and/or removable component of a thermocycler.

In one embodiment, a multichamber cartridge comprises a rotating filter membrane comprising a plurality of channels in connection with one or more tubes or chambers of the cartridge, wherein the plurality of channels are opened or closed by rotating the rotating filter membrane. In one embodiment, the rotating filter membrane is in fluid connection with a receiving tube. In one embodiment, the rotating filter membrane is in fluid connection with one or more buffer solution tubes. In one embodiment, the rotating filter membrane is in fluid connection with a waste chamber. In another embodiment, the rotating filter member is in fluid connection with a blistered chamber. In another embodiment, the rotating filter membrane is in fluid connection with the first chamber or cold chamber. In yet another embodiment, the rotating filter membrane is in fluid connection with the second or hot chamber. In further embodiments, the rotating filter membrane is in fluid connection with a third, fourth, fifth, sixth, seventh, eighth, ninth, tenth chamber or any combination thereof. In one embodiment, the rotating filter membrane is a disposable and/or removable component of a thermocycler.

In one embodiment, a multichamber cartridge comprises a waste chamber or alternatively, a waste tube. The waste chamber holds waste from one or more tubes and/or one or more chambers of a multichamber cartridge. In some embodiments, the waste chamber holds volumes up to about 10 mL, up to about 8 mL, up to about 7 mL, up to about 6 mL, up to about 5 mL, up to about 4 mL, up to about 3 mL, up to about 2 mL, up to about 1 mL, or up to about 0.5 mL. In one embodiment, the waste chamber is a disposable and/or removable component of a thermocycler.

In one embodiment, a multichamber cartridge comprises a blistered chamber, for example, a blistered chamber as previously described. In one embodiment, the blistered chamber is in fluid connection with a rotating filter membrane. In another embodiment, the blistered chamber is in fluid connection with a first or cold chamber. In another embodiment, the blistered chamber is in fluid connection with a second or hot chamber. In another embodiment, the blistered chamber is in fluid connection with a third, fourth, fifth, sixth, seventh, eighth, ninth, tenth chamber or any combination thereof. In some implementation, the blistered chamber is compressed by an actuator to move contents to other chambers of the cartridge, for example, the first or second chambers. In one instance, the actuator is a component of a thermocycler provided herein. In one embodiment, the blistered chamber is a disposable and/or removable component of a thermocycler. The blistered chamber, in many instances, comprises reagents useful for sample preparation and/or performing a thermocycling reaction. Such reagents are manufactured with the cartridge or added by an end-user prior to performing a thermocycling reaction. Suitable reagents include, without limitation, Lysozyme and Proteinase K. In one embodiment, the reagents are formulated as a solution or a powder. In one embodiment, one or more reagents of the blistered chamber are activated by a heater in a heat activation step. In an additional embodiment, the blister chamber is in contact with a heater.

In an exemplary embodiment, a fluid comprising a sample is moved from one chamber to another, e.g., between a first and second chamber, by deforming one chamber with pressure from one or more actuators as previously described.

In one embodiment, a multichamber cartridge comprises a window or cuvette to view a fluid in the cartridge. In an exemplary embodiment, the window is an optical viewing window useful for fluorescent detection. The optical viewing window is comprised of optically transparent material for receiving and transmitting light.

The chambers of the multichamber cartridge are of any size suitable for their respective functions in an amplification reaction. For example, any chamber of the multichamber cartridge holds a volume of solution (e.g., sample reaction solution, buffer solution, waste solution, blistered chamber solution) from about 5 µL to about 5 mL. Similarly, the tubes of the multichamber cartridge are of any size to accommodate volumes from about 5 µL to about 5 mL. In one embodiment, one or more tubes, chambers and/or other multichamber components are operably connected to or attached to the multichamber cartridge. In various implementations, any number of components, e.g., tube, chamber, are removable or non-removable components.

In one embodiment, one or more chambers or components of a cartridge provided herein is adapted for nucleic acid extraction, nucleic acid purification, nucleic acid detection and/or nucleic acid amplification.

In one embodiment, the multichamber cartridge is a disposable portion of a thermocycler. In another embodiment, the multichamber cartridge is useful with a thermocycler described herein. In another embodiment, the multichamber cartridge is a laminated disposable cartridge.

In one embodiment, the multichamber cartridge comprises plastic injected polycarbonate material. In one embodiment, the multichamber cartridge comprises Kapton laminate. In another embodiment, the multichamber cartridge comprises PSA. In a further embodiment, the multichamber cartridge comprises PET laminate. Additional multichamber cartridge materials include, without limitation, cardboard, plastic and paper.

In one embodiment, one or more components of the multichamber cartridge are labeled. For example, a label provides information that is readable to a human or machine to provide information relating to a sample. A label includes a scannable barcode.

In one aspect, fluid is transferred between one or more chambers of a cartridge provided herein and one or more chambers and/or cartridge components provided herein, by mechanical actuation. In other embodiments, fluid is transferred without using movable components of a cartridge and/or thermocycler. In some embodiments, fluid is transferred using magnetic means, for example, by using magnetic fluids or magnetic beads.

In various implementations, one or more chambers of the cartridges described herein are pre-loaded with reagents. Reagents include liquids, solids, gases or combinations thereof. In an additional embodiment, one or more chambers of the cartridge comprises at least one opening to allow for the addition or removal of a sample. In one embodiment, the opening is sealed or otherwise closed to maintain the sample in the chamber. In another or additional embodiments, a chamber is initially empty so as to serve, for example, as a waste, mixing and/or detection chamber prior to, during or after a thermocycling reaction. Reagents include those which are formulated as a pellet or tablet, or are lyophilized. In an example, reagents are useful for sample preparation (e.g., immobilization), amplification (e.g., primers), or detection (e.g., probes). In one embodiment, a solid reagent is re-suspended with a fluid, for example, one provided by an adjacent chamber or tube. In an additional embodiment, a chamber comprises cryoprotectants or preserving agents such as disaccharides (e.g., trehalose, sucrose).

In various implementation, one or more chambers of the cartridge are useful for processing amplified nucleic acids after completion of thermocycling. For example, a chamber comprises one or more reagents, either pre-loaded or provided by an end-user, for performing a restriction digest on amplified nucleic acids. In another or additional embodiment, a chamber comprises one or more reagents, either pre-loaded or provided by an end-user, for performing a ligation reaction.

A cartridge is loaded with a sample by manual, automated, or manual and automated methods. Sample loading methods include, without limitation, pipetting, injection, spotting, and syringe drawing.

Figure 16:
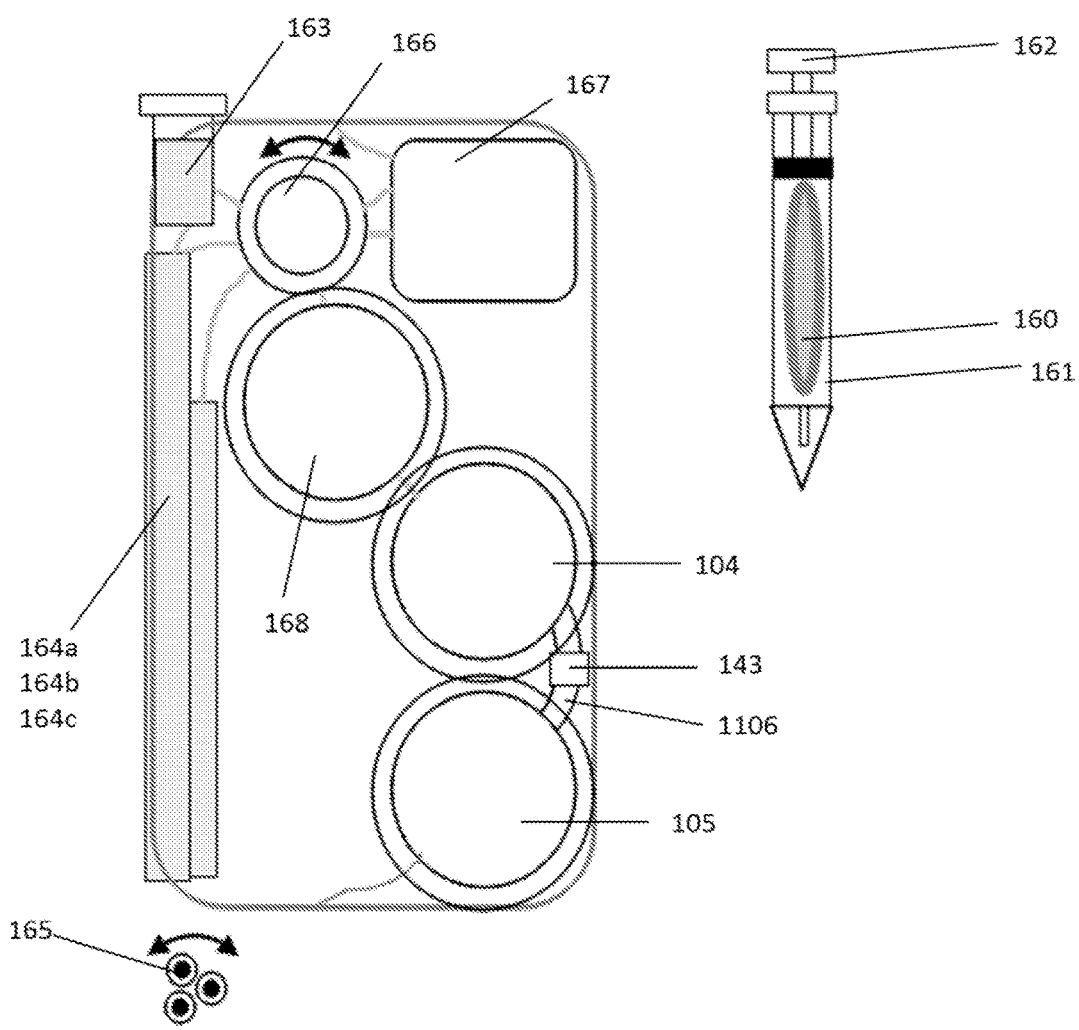
FIG. 16 shows an embodiment of a multichamber cartridge.

An exemplary multichamber cartridge is provided in FIG. 16. The multichamber cartridge in this embodiment comprises a first chamber or cold chamber 104 for holding a fluid at a first average temperature and a second chamber or hot chamber 105 for holding a fluid at a second average temperature. The first chamber 104 and the second chamber 105 is in fluid connection via a connecting channel 106. The connecting channel 106 comprises a viewing window 143 for fluid detection. In one embodiment, the window is an optical viewing window for fluorescent detection.

The multichamber cartridge of FIG. 16 further comprises a swab collection tube 161 for holding a sample 160, wherein the swab collection tube optionally comprises a plunger 162. The sample, and optionally a buffer, is transferred to a receiving tube 163 via the depression of the plunger 162.

The multichamber cartridge of FIG. 16 further comprises three buffer solution tubes, 164a, 164b and 164c. In one embodiment, the buffer solution tubes have a volume from about 10 µL to about 2 mL. In one embodiment, buffer solution tube 164a has a volume of about 200 µL, buffer solution tube 164b has a volume of about 200 µL and buffer solution tube 164c has a volume of about 300 µL. The buffer solutions are transferred to a rotating filter membrane 166 by a rotating plunger 165. The rotating filter membrane comprises a plurality of channels in connection with the receiving tube 163, at least one buffer solution tube 164, a waste chamber 167, and a blistered chamber 168, wherein the plurality of channels are opened or closed by rotating the rotating filter membrane. The waste chamber 167 functions to collect waste solution from other components of the cartridge. The cartridge embodied in FIG. 16 further comprises a blistered chamber 168. In one example, the blistered chamber is 12 mm in diameter and 0.5 mm high. In one embodiment, one or more reagents are stored in this chamber, for example Lysozyme and/or Proteinase K.

In one embodiment, a rotating filter membrane 166 controls release of a sample from the receiving tube 163 to a blister chamber 168 and/or a waste chamber 167. In one embodiment, a rotating filter membrane 166 controls release of a buffer from one or more buffer tubes 165 to a blister chamber 168 and/or a waste chamber 167.

Cartridge-Based Thermocycler Methods

In one aspect, provided herein are cartridge-based thermocyclers and thermocycling systems comprising one or more cartridges. In one embodiment, a thermocycler described herein is configured to perform a thermocycling reaction with at least two cartridges at the same time. In one example, one cartridge comprises a reference sample and another cartridge comprises a test sample. For instance, in a diagnostic assay, a reference or control sample is amplified under the same conditions as a test sample.

The cartridge-based thermocyclers provided herein allow for the quantitative or qualitative detection of a target nucleic acid in a sample. For example, during a nucleic acid amplification reaction, a target component in a sample is detected when one or more detectably labeled probes hybridize to the target and to the amplification products thereof. In many instances, the detection of the target is indicative of a disease presence in the sample, for example, when the target is a nucleic acid from an infectious agent. In another instance, the expression level of a target nucleic acid in a sample is quantified during a PCR reaction. In some instances, expression level is indicative of a disease state or a correlation to a disease state. For example, differential expression of a nucleic acid expression product, e.g., RNA, as compared to a reference expression level, is indicative of a disease state.

In another aspect, provided herein are thermocycling systems useful for forensic applications, for example, in genetic fingerprinting.

In another aspect, provided herein are thermocycling systems useful for DNA sequencing.

In exemplary embodiments, the thermocycling systems provided herein can be employed to detect and/or quantify two or more different nucleic acids in a sample. For example, the nucleic acids can be quantified according to the rate at which they can be amplified detectably from the sample by an amplification reaction in which the nucleic acids are copied exponentially and/or linearly. Any suitable amplification approach can be used, including PCR. In some embodiments, probes for different nucleic acid targets in a sample are labeled with a different detectable label (e.g., fluorescent label). Hybridization of a probe to the target can produce a change in light emission from the detectable label.

A suitable assay that can quantify nucleic acids according to the rate of change in light emission is exemplified by a TaqMan® assay (Applied Biosystems). The cartridges, thermocyclers, and systems provided herein are useful for such thermocycling reactions. Thermocycling reactions include nucleic acid amplification reactions. Such reactions include, without limitation, PCR, real-time PCR, allele-specific PCR, SNP genotyping, assembly PCR (e.g. nucleic acid synthesis), asymmetric PCR, helicase-dependent amplification, ligation mediated PCR, quantitative PCR, and reverse transcription PCR. In one embodiment, the cartridges, thermocyclers and systems provided herein are used for multiplex-PCR.

The detection and/or measurement of amplification products are performed at reaction completion or in real time (i.e., during reaction), where real time includes continuous or discontinuous measurement and/or detection. If the measurement of accumulated amplified product is performed after amplification is complete, the labeled probes can be added after the amplification reaction. Alternatively, probes are added to the reaction prior to or during the amplification reaction.

In another aspect, provided herein are cartridge-based thermocyclers for performing real-time PCR. Real-time PCR, in various implementations, is useful to simultaneously amplify and detect or quantify a nucleic acid molecule in a sample. In one embodiment, amplified nucleic acid molecules are detected using detectable dyes, e.g., fluorescent dyes, that intercalate with DNA. In another embodiment, amplified nucleic acid molecules are detected using nucleic acid probes comprising detectable labels. In one embodiment, a probe comprises a plurality of detectable labels. Detectable labels are naturally and/or artificially occurring. Naturally occurring labels include green fluorescent protein (GFP), phycobiliproteins, luciferase, and/or their many variations, among others. Artificially occurring labels include, for example, rhodamine, fluorescein, FAM™/SYBR® Green I, VIC®/JOE, NED™/TAMRA™/Cy3™, ROX™/Texas Red®, Cy5™, among others. Suitable natural and artificial labels are disclosed in the following publication, among others, which is incorporated herein by reference: Richard P. Haugland, Handbook of Fluorescent Probes and Research Chemicals (6th ed. 1996). In some embodiments, a fluorescently labeled probe is active only in the presence of a target molecule, for example, a specific nucleic acid sequence, so that a fluorescent response from a sample signifies the presence of the target molecule. In exemplary embodiments, a probe is a hybridization probe comprising an oligonucleotide which hybridizes to a target nucleic acid sequence that is complementary to the oligonucleotide probe sequence.

In some embodiments, a probe is a molecular beacon. A molecular beacon probe, as described herein, includes a single-stranded oligonucleotide in which the bases on the 3' and 5' ends are complementary, forming a stem. A molecular beacon probe forms a hairpin structure at temperatures at and below those used to anneal the oligonucleotide to a target. In some embodiments, the molecular beach probe forms a hairpin structure at temperatures below about 60° C. The double-helical stem of the hairpin brings a fluorophore (or other label) attached to the 5' end of the probe in proximity to a quencher attached to the 3' end of the probe. The probe does not fluoresce (or otherwise provide a signal) in this conformation. If a probe is heated above the temperature needed to melt the double stranded stem apart, or the probe hybridizes to a target nucleic acid that is complementary to the sequence within the single-strand loop of the probe, the fluorophore and the quencher are separated, and the fluorophore fluoresces in the resulting conformation. Therefore, in a series of nucleic acid amplification cycles the strength of the fluorescent signal increases in proportion to the amount of the molecular beacon that is hybridized to the target, when the signal is read at the annealing temperature. Molecular beacons of high specificity, having different loop sequences and conjugated to different fluorophores, can be selected in order to monitor increases in amplicons that differ by as little as one base.

During a real-time PCR reaction, fluorescence intensity is monitored in real time. A key element in the measurement is to identify the thermal cycle number at which the label emission intensities rise above background noise and starts to increase, preferably exponentially. This cycle number is called the threshold cycle, $C_t$. The $C_t$ value is inversely proportional to the number of starting copies of the DNA sample in the original PCR solution. Knowing $C_t$, the quantity of the DNA to be detected in the sample can be determined.

In one aspect, provided herein are thermocycling systems useful for the identification and management of a disease state. For example, DNA fragments comprising a gene or expression product thereof can be amplified and detected using one or more detectably labeled probes as previously described. In one embodiment, a detectably labeled probe comprising a sequence indicative of a disease state comprises a distinct fluorophore which is detected using an optical detector. For example, a sequence indicative of a disease state comprises one or more mutations. In some embodiments, the presence of a sequence of nucleic acid is identified using a thermocycling system described herein. In one example, a nucleic acid sequence from an infectious disease agent (e.g., bacteria, virus) is present in a human or environmental sample. The nucleic acid sequence is amplified and detected by hybridization with a detectably labeled probe. In some embodiments, a plurality of dectably labeled probes are provided in an amplification reaction, wherein unique combinations of probes are indicative of a disease state, allowing for a multiplex reaction to be performed within one cartridge. In other embodiments, a plurality of cartridges are used in a thermocycling system provided herein.

In another aspect, provided herein is a method for monitoring a thermocycling reaction, the method comprising a) providing a thermocycler comprising a first chamber for holding fluid at a first average temperature and a second chamber for holding the fluid at a second average temperature, wherein the second chamber is in fluid communication with the first chamber, b) introducing a sample into either the first chamber or the second chamber, wherein the sample comprises a nucleic acid molecule and one or more detectably labeled probes configured to hybridize to the nucleic acid molecule; c) transferring the sample from the first chamber to the second chamber; and d) measuring a detectable signal emitting from the sample in response to a stimulus using an optical detector. In some embodiments, the detectable signal comprises both a signal correlating to nucleic acid amplification and a signal correlating to noise. In some instances, the signal correlating to nucleic acid amplification is indicative of a quantity of amplified nucleic acid in the sample. In some embodiments, the signal correlating to nucleic acid amplification is distinguishable from the signal correlating to noise.

EXAMPLES

Example 1: Thermocycler Cartridge

A cartridge of a cartridge-based thermocycler comprises a four-layered laminated structure having two chambers in fluid connection via a connecting channel. One or both of the chambers is connected to one or more addition channels to allow for filling a chamber with fluid or extracting fluid from a chamber. The structure is manufactured with or without an optical window. If the structure is manufactured without the optical window, an optical detection signal can be read through a top layer of the structure, preferably over a chamber of the cartridge. The cartridge comprises a laminate layer having a 50.8 µm thick PET film, a laminate layer having a 127 µm thick 3M 96042 Double-Coated Silicone Adhesive layer, another laminate layer having a 127 µm thick 3M 96042 Double-Coated Silicone Adhesive layer, and a laminate layer having a 50.8 µm thick Kapton® MT film. The thickness of each chamber is 254 µM. A working example of this cartridge is shown in FIG. 14A.

Example 2: Method of Nucleic Acid Amplification Using a Cartridge-Based Thermocycler A cartridge as described in Example 1 is part of a thermocycling system comprising a thermocycling instrument. The thermocycling instrument comprises two heater blocks, wherein one heater block provides heat at a first average temperature to the first chamber and the second heater block provides heat at a second average temperature to the second chamber. The thermocycling instrument comprises two actuators, wherein one actuator provides pressure to one chamber and the second actuator provides pressure to the second chamber, and wherein said pressure is sufficient to propel a fluid from one chamber into another chamber.

A 50 µL nucleic acid amplification reaction was prepared comprising 21.25 µL of $10^5$ DNA/mL B. Afro, 25 µL TaqMan® Master Mix, 1.25 µL of $10^5$ µM FAM probe, 1.25 µL of 36 µM B. Atro forward primer and 1.25 µL of 36 µM B. Afro reverse primer. The reaction mixture was added to a first chamber of the cartridge through a channel. The cartridge was placed in a slot of the thermocycling instrument and a thermocycling program was set. Thermocycling conditions were: 95° C. for 30 seconds; 55 cycles of 95° C. for 10 seconds and 60° C. for 10 seconds. During the thermocycling reaction, actuators of the instrument applied pressure alternatively to each chamber, propelling the reaction mixture from one chamber to another through a connecting channel, while each chamber was maintained at an average temperature by each heater. One chamber was maintained at an average temperature of 60° C. and the other chamber was maintained at an average temperature of 95° C.

The reaction was monitored in real-time by measuring fluorescence intensity as a function of cycle number. The fluorescence intensity data is shown in FIG. 14B. The $C_t$ value was 28.4 for this reaction. The time to reach 30 cycles was 10 minutes, 30 seconds (10 minutes of cycling and a 30 second hot start).

Example 3: Molecular Diagnosis of a Disease Using Real-Time PCR Performed with a Cartridge-Based Thermocycler This example describes a quantitative real-time RT-PCR assay for the detection of an infectious disease from a patient sample, in this instance serum. This assay targets a nucleic acid region specific in sequence for the disease, in this case a virus, and utilizes fluorescently labeled probes for detection. This assay is similarly performed utilizing a plurality of probes targeting additional infectious diseases in a multiplexed assay. Alternatively, this assay is performed for serotyping a disease by utilizing a plurality of probes targeting different serotypes of the disease. These optional multiplexed assays are performed in a single cartridge of a thermocycler described herein.

The real-time RT-PCR reaction is performed using a thermocycler described in Examples 1 and 2, which is operably attached to an optical detector, and a commercial qRT-PCR kit (SuperScript One-Step qRT-PCR, Life Technologies). The connecting channel of the cartridge has an optical window to allow for excitation light from the optical detector to reach the sample and to allow for emission light from the reaction mixture to reach the detector. Thus, during the thermocycling reaction, as the detectably labeled probe hybridizes to amplification products, the optical detector records fluorescence signals in real-time.

The real-time RT-PCR reaction mixture comprises a forward primer and reverse primer designed to amplify a target nucleic acid region of the virus. Nucleic acids are extracted from serum samples of a patient using the QIAamp Viral RNA Mini Kit (Qiagen) using recommended procedures. The extracted nucleic acids are added to the reaction mixture at concentrations between about 1 pg to about 1 µg total RNA. A TaqMan® probe is added to the final PCR reaction. The probe is added to the reaction via a blistered chamber or directly to the reaction mixture.

Thermocycling conditions are: 50° C. for 15 minutes (RT step); 95° C. for 2 minutes; 40 cycles of 95° C. for 2 seconds and 60° C. for 2 seconds. The total cycle time is less than about 25 minutes and the PCR time is less than about 10 minutes.

The reaction is monitored in real-time using an optical detector to detect fluorescence of the detectably labeled probe hybridized to amplified target nucleic acids.

A positive diagnosis of the infectious disease is considered when a sample has a $C_t$ value less than about 35.

This diagnosis is performed as a point-of-care assay. As an example, the sample is whole blood which is processed in a sample processing cartridge prior to addition to the thermocycling cartridge. Alternatively, the sample is processed in one or more chambers of a thermocycling cartridge as a first step in a thermocycling reaction.

Example 4: Cartridge Kit

A disposable portion of a thermocycler is provided in the form of a single cartridge. The cartridge comprises at least two chambers connected by a channel to allow fluid to flow between the chambers. The chambers are constructed from suitable material to allow for compression. One or both chambers is connected, e.g., through a channel, to one or more ports, to allow for the addition or removal of a liquid, gas, solid or combination thereof. The cartridge is customizable with additional elements.

One additional element is a means to allow for the optical detection of a substance within the cartridge. This means includes an optical window located in a chamber or connecting channel. Another means is a cuvette connected by a fluid path to one or more chambers. The cartridge is configured for optical detection in real-time or at one or more time points during use.

Another additional element is a blistered chamber. The blistered chamber is similarly customizable to comprise reagents for use in a thermocycling reaction. Alternatively, the blistered chamber is supplied empty, allowing for an end-user to add reagents.

The cartridge is optionally provided with an instrument in a thermocycler system. The instrument is able to act on all or a portion of the cartridge and such actions are programmable. Such actions include moving a fluid between chambers, opening and closing channels between chambers, providing a barrier between chambers, heating or cooling a chamber, and any combination thereof. The instrument is configured to be provided with, or configured to be operably connected to, an optical detector.

It is to be understood that the terminology used herein is used for the purpose of describing specific embodiments, and is not intended to limit the scope of the present invention. It should be noted that as used herein, the singular forms of "a", "an" and "the" include plural references unless the context clearly dictates otherwise. In addition, unless defined otherwise, all technical and scientific terms used herein have the same meaning as commonly understood by one of ordinary skill in the art to which this invention belongs.

While preferable embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for performing polymerase chain reaction (PCR), comprising:
    conveying a sample having a starting volume of at least 50 µL into a first chamber portion of an amplification module, the first chamber portion having a first average temperature;
    producing a flow of the sample from the first chamber portion to a second chamber portion of the amplification module, the second chamber portion having a second average temperature, the second average temperature different than the first average temperature such that the sample is thermally cycled when moved from the first chamber portion to the second chamber portion, the amplification module being constructed from a plurality of layers to define the first chamber portion and the second chamber portion, the plurality of layers including at least a top layer, a bottom layer, a first adhesive layer coupled to the top layer, and a second adhesive layer coupled to the bottom layer, wherein at least one layer selected from the group consisting of the top layer and the bottom layer, comprises poly (4,4'-oxydiphenylene-pyromellitimide); and
    completing the PCR of the sample by repeatedly flowing the sample between the first chamber portion and the second chamber portion.

2. The method of claim 1, further comprising completing the PCR amplification within a total thermocycling time of less than about 10 minutes.

3. The method of claim 1, further comprising filling the first chamber portion with fluid from an ancillary chamber.

4. The method of claim 1, further comprising detecting PCR amplification by monitoring the first chamber portion, the second chamber portion or a channel between the first chamber portion and the second chamber portion.

5. The method of claim 1, further comprising heating the first chamber portion or the second chamber portion using one-sided heating.

6. The method of claim 1, further comprising heating the first chamber portion or the second chamber portion using two-sided heating.

7. The method of claim 1, wherein the PCR efficiency is at least about 92%.

8. The method of claim 1, wherein the sample is flowed between the first chamber portion and the second chamber portion at least 20 times.

9. The method of claim 1, wherein the sample is flowed between the first chamber portion and the second chamber portion at least 30 times.

10. The method of claim 1, wherein the sample is flowed between the first chamber portion and the second chamber portion at least 40 times.

11. The method of claim 1, wherein the sample is cycled from the first chamber portion to the second chamber portion and back to the first chamber portion with a cycle time of less than about 15 seconds.

12. The method of claim 11, wherein the cycle time is less than about 10 seconds.

13. A method for performing polymerase chain reaction (PCR), comprising:
    conveying a sample having a starting volume of at least 50 µL into an amplification module having a first portion having and a second portion, the amplification module being constructed from a plurality of layers to define the first portion and the second portion, the plurality of layers including at least a top layer, a bottom layer, a first adhesive layer coupled to the top layer, and a second adhesive layer coupled to the bottom layer, wherein at least one layer selected from the group consisting of the top layer and the bottom layer, comprises poly (4,4'-oxydiphenylene-pyromellitimide);
    heating the first portion of the amplification module to a first average temperature;
    heating the second portion of the amplification module to a second average temperature, the second average temperature different than the first average temperature;
    producing a flow of the sample from the first portion to the second portion of the amplification module such that the sample is thermally cycled when moved from the first portion to the second portion, and such that the sample transitions from the first average temperature to substantially the second average temperature at a rate of 10 µL° C./second or more; and
    completing the PCR of the sample by repeatedly flowing the sample between the first portion and the second portion at least 20 times.

14. The method of claim 13, wherein the sample is flowed between the first portion and the second portion at least 30 times.

15. The method of claim 13, wherein the sample is flowed between the first portion and the second portion at least 40 times.

16. The method of claim 13, further comprising completing the PCR amplification within a total thermocycling time of less than about 4 minutes.

17. The method of claim 13, further comprising filling the first portion with fluid from an ancillary chamber.

18. The method of claim 13, further comprising detecting PCR amplification by monitoring any of the first portion of the amplification module, the second portion of the amplification module, or a channel between the first portion and the second portion.

19. The method of claim 13, further comprising heating the first portion of the amplification module or the second portion of the amplification module using one-sided heating.

20. The method of claim 13, wherein the PCR efficiency is at least about 92%.

21. The method of claim 19, wherein the amplification module includes a first heater and a second heater, the first heater coupled to a substrate and aligned with the first portion, the second heater coupled to the substrate and aligned with the second portion, the second heater separated from the first heater by an air gap.

22. The method of claim 13, wherein the first portion and the second portion are fluidically coupled via a channel through which the sample flows from the first portion to the second portion.

\* \* \* \* \*